(12) United States Patent
Levy et al.

(10) Patent No.: US 10,117,648 B2
(45) Date of Patent: Nov. 6, 2018

(54) SURGICAL FASTENER DELIVERY AND LOCKING MECHANISM

(71) Applicant: Via Surgical Ltd., Moshav Amirim (IL)

(72) Inventors: Arie Levy, Shoham (IL); Yehonatan Levin, Amirim (IL); Lena Levin, Moshav Amirim (IL); Ofek Levin, Moshav Amirim (IL)

(73) Assignee: Via Surgical Ltd., Moshav Amirim (IL)

( * ) Notice: Subject to any disclaimer, the term of this patent is extended or adjusted under 35 U.S.C. 154(b) by 393 days.

(21) Appl. No.: 15/132,861

(22) Filed: Apr. 19, 2016

(65) Prior Publication Data

US 2016/0310146 A1    Oct. 27, 2016

Related U.S. Application Data

(60) Provisional application No. 62/151,631, filed on Apr. 23, 2015.

(51) Int. Cl.
  *A61B 17/064*    (2006.01)
  *A61B 17/068*    (2006.01)
  (Continued)

(52) U.S. Cl.
  CPC ...... *A61B 17/0644* (2013.01); *A61B 17/0485* (2013.01); *A61B 17/068* (2013.01);
  (Continued)

(58) Field of Classification Search
  CPC . A61B 17/064; A61B 17/0642; A61B 17/068; A61B 17/0057; A61B 17/0404;
  (Continued)

(56) References Cited

U.S. PATENT DOCUMENTS 2,881,762 A    4/1959 Lowrie
3,212,502 A    10/1965 Myers
(Continued)

FOREIGN PATENT DOCUMENTS

CN    101507626 A    8/2009
CN    101969859 A    2/2011
(Continued)

OTHER PUBLICATIONS

Gillian, et al., 2002, Laparoscopic Incisional and Ventral Hernia Repair (LIVH): An Evolving Outpatient Technique, USLS 6(4):315-322.
International Search Report and Written Opinion dated Oct. 29, 2013, for International Patent Application No. PCT/IB2013/000647, filed Feb. 15, 2013 (17 pages).
International Search Report and Written Opinion dated Jun. 20, 2013 in related international application PCT/IB12/02957, filed Dec. 17, 2012 (10 pages).
(Continued)

*Primary Examiner* — Scott A. Smith
(74) *Attorney, Agent, or Firm* — Brown Rudnick LLP; Thomas C. Meyers

(57) ABSTRACT

The invention provides a fastening device for laparoscopic hernia repair. The coordinated operation of two insertion members stabilizes a fastener during closure and locking to ensure that the fastener is locked in the intended location before the device releases from the fastener. One of the insertion members includes a pair of prongs that exhibit a closed configuration when they are disposed in a recess at an end of the fastener. The fastener has a hook at one end and a loop at the other end. The insertion members push the fastener out from the device and through the tissue. A curvature in at least one of the insertion members pushes the hook through the loop all while the prongs are in the recess in the fastener, thereby stabilizing the fastener with respect to the device.

22 Claims, 21 Drawing Sheets

(51) Int. Cl.
*A61B 17/04* (2006.01)
*A61B 17/072* (2006.01)
*A61B 17/06* (2006.01)
*A61B 17/00* (2006.01)

(52) U.S. Cl.
CPC ....... *A61B 17/0057* (2013.01); *A61B 17/0469* (2013.01); *A61B 17/0487* (2013.01); *A61B 17/064* (2013.01); *A61B 2017/0409* (2013.01); *A61B 2017/0645* (2013.01); *A61B 2017/06176* (2013.01); *A61B 2017/07214* (2013.01); *A61B 2017/07278* (2013.01); *A61F 2220/0016* (2013.01)

(58) Field of Classification Search
CPC ............ A61B 17/0482; A61B 17/0487; A61B 17/0485; A61B 17/0644; A61B 17/072; A61B 17/07207; A61B 2017/07278; A61B 2017/07214; A61B 2017/0409; A61B 2017/06176; A61B 2017/0475
USPC .............. 227/19, 175.1, 175.2, 176.1, 180.1; 606/139, 142, 143, 151, 153, 219
See application file for complete search history.

(56) References Cited

U.S. PATENT DOCUMENTS

| | | |
|---|---|---|
| 4,069,825 A | 1/1978 | Akiyama |
| 4,235,238 A | 11/1980 | Ogiu et al. |
| 4,391,402 A | 7/1983 | Campbell et al. |
| 4,394,864 A | 7/1983 | Sandhaus |
| 4,458,835 A | 7/1984 | Li et al. |
| 4,536,933 A | 8/1985 | Furutsu |
| 4,809,695 A | 3/1989 | Gwathmey et al. |
| 4,900,303 A | 2/1990 | Lemelson |
| 4,950,285 A | 8/1990 | Wilk |
| 5,037,433 A | 8/1991 | Wilk et al. |
| 5,104,395 A | 4/1992 | Thornton et al. |
| 5,123,913 A | 6/1992 | Wilk et al. |
| 5,174,487 A | 12/1992 | Rothfuss et al. |
| 5,222,961 A | 6/1993 | Nakao et al. |
| 5,242,457 A | 9/1993 | Akopov et al. |
| 5,330,488 A | 7/1994 | Goldrath |
| 5,356,064 A | 10/1994 | Green et al. |
| 5,364,002 A | 11/1994 | Green et al. |
| 5,364,022 A | 11/1994 | Ganz |
| 5,425,489 A | 6/1995 | Shichman et al. |
| 5,445,167 A | 8/1995 | Yoon et al. |
| 5,582,616 A | 12/1996 | Bolduc et al. |
| 5,626,587 A | 5/1997 | Bishop et al. |
| 5,662,662 A | 9/1997 | Bishop et al. |
| 5,728,113 A | 3/1998 | Sherts |
| 5,830,221 A | 11/1998 | Stein et al. |
| 5,895,395 A | 4/1999 | Yeung |
| 5,916,146 A | 6/1999 | Allotta et al. |
| 5,964,394 A | 10/1999 | Robertson |
| 5,968,044 A | 10/1999 | Nicholson et al. |
| 6,156,039 A | 12/2000 | Thal |
| 6,306,149 B1 | 10/2001 | Meade |
| 6,350,269 B1 | 2/2002 | Shipp et al. |
| 6,425,900 B1 | 7/2002 | Knodel et al. |
| 6,447,524 B1 | 9/2002 | Knodel et al. |
| 6,494,886 B1 | 12/2002 | Wilk et al. |
| 6,530,933 B1 | 3/2003 | Yeung et al. |
| 6,607,542 B1 | 8/2003 | Wild |
| 6,638,286 B1 | 10/2003 | Burbank et al. |
| 6,733,506 B1 | 5/2004 | McDevitt et al. |
| 7,004,970 B2 | 2/2006 | Cauthen, III et al. |
| 7,125,413 B2 | 10/2006 | Grigoryants et al. |
| 7,141,057 B2 | 11/2006 | Burbank et al. |
| 7,338,502 B2 | 3/2008 | Rosenblatt |
| 7,398,908 B2 | 7/2008 | Holsten et al. |
| 7,431,730 B2 | 10/2008 | Viola |
| 7,591,783 B2 | 9/2009 | Boulais et al. |
| 7,594,923 B2 | 9/2009 | Fallin et al. |
| 7,625,386 B2 | 12/2009 | Abe et al. |
| 7,704,261 B2 | 4/2010 | Sakamoto et al. |
| 7,708,180 B2 | 5/2010 | Murray et al. |
| 7,776,066 B2 | 8/2010 | Onuki et al. |
| 7,842,047 B2 | 11/2010 | Modesitt et al. |
| 7,850,701 B2 | 12/2010 | Modesitt et al. |
| 7,913,891 B2 | 3/2011 | Doll et al. |
| 7,918,868 B2 | 4/2011 | Marshall et al. |
| 7,959,640 B2 | 6/2011 | Kantsevoy et al. |
| 7,967,831 B2 | 6/2011 | Rosenberg et al. |
| 8,034,076 B2 | 10/2011 | Criscuolo et al. |
| 8,070,035 B2 | 12/2011 | Holsten et al. |
| 8,075,572 B2 | 12/2011 | Stefanchik et al. |
| 8,091,756 B2 | 1/2012 | Viola |
| 8,114,099 B2 | 2/2012 | Shipp |
| 8,132,705 B2 | 3/2012 | Viola et al. |
| 8,177,795 B2 | 5/2012 | Niese et al. |
| 8,211,126 B2 | 7/2012 | Yeh et al. |
| 8,216,272 B2 | 7/2012 | Shipp |
| 8,277,373 B2 | 10/2012 | Maahs et al. |
| 8,282,670 B2 | 10/2012 | Shipp |
| 8,343,176 B2 | 1/2013 | Criscuolo et al. |
| 8,535,339 B2 | 9/2013 | Levin et al. |
| 8,603,118 B2 | 12/2013 | Yeh et al. |
| 8,814,885 B2 | 8/2014 | Domingo |
| 8,961,530 B2 | 2/2015 | Bhatnagar et al. |
| 9,724,088 B2 * | 8/2017 | Domingo ........... A61B 17/0469 |
| 9,782,162 B2 * | 10/2017 | Levin ................. A61B 17/0469 |
| 9,872,727 B2 * | 1/2018 | Motai ..................... A61B 18/14 |
| 2001/0046646 A1 | 11/2001 | Koba |
| 2002/0068951 A1 | 6/2002 | Burbank et al. |
| 2002/0107530 A1 | 8/2002 | Sauer et al. |
| 2003/0139752 A1 | 7/2003 | Pasricha et al. |
| 2003/0208209 A1 | 11/2003 | Gambale et al. |
| 2004/0098045 A1 | 5/2004 | Grafton et al. |
| 2004/0138681 A1 | 7/2004 | Pier |
| 2004/0204723 A1 | 10/2004 | Kayan |
| 2006/0235443 A1 | 10/2006 | Huitema et al. |
| 2007/0045379 A1 | 3/2007 | Shelton |
| 2007/0112361 A1 | 5/2007 | Schonholz et al. |
| 2007/0179509 A1 | 8/2007 | Nagata et al. |
| 2007/0250064 A1 | 10/2007 | Darois et al. |
| 2007/0270637 A1 | 11/2007 | Takemoto et al. |
| 2008/0091219 A1 | 4/2008 | Marshall et al. |
| 2008/0097523 A1 | 4/2008 | Bolduc et al. |
| 2008/0110958 A1 | 5/2008 | McKenna et al. |
| 2008/0255591 A1 | 10/2008 | Harada et al. |
| 2009/0018554 A1 | 1/2009 | Thorne et al. |
| 2009/0114233 A1 | 5/2009 | Edoga et al. |
| 2009/0206144 A1 | 8/2009 | Doll et al. |
| 2009/0209980 A1 | 8/2009 | Harris |
| 2009/0222083 A1 | 9/2009 | Nguyen et al. |
| 2009/0259251 A1 | 10/2009 | Cohen |
| 2010/0016870 A1 | 1/2010 | Campbell |
| 2010/0069930 A1 | 3/2010 | Roslin et al. |
| 2010/0094248 A1 | 4/2010 | Nguyen et al. |
| 2010/0145361 A1 | 6/2010 | Francischelli et al. |
| 2010/0160931 A1 | 6/2010 | Karpiel et al. |
| 2010/0191283 A1 | 7/2010 | Foerster et al. |
| 2010/0292710 A1 | 11/2010 | Daniel et al. |
| 2010/0318107 A1 | 12/2010 | Mizrahy et al. |
| 2010/0327042 A1 | 12/2010 | Amid et al. |
| 2010/0331863 A2 | 12/2010 | Saliman et al. |
| 2011/0071548 A1 | 3/2011 | Yeh et al. |
| 2011/0092992 A1 | 4/2011 | Darois et al. |
| 2011/0098728 A1 | 4/2011 | McDevitt et al. |
| 2011/0118757 A1 | 5/2011 | Pierce |
| 2011/0130774 A1 | 6/2011 | Criscuolo et al. |
| 2011/0178534 A1 | 7/2011 | Whitman et al. |
| 2011/0319932 A1 | 12/2011 | Avelar et al. |
| 2012/0016389 A1 | 1/2012 | Kantsevoy et al. |
| 2012/0089157 A1 | 4/2012 | Forsell |
| 2012/0109132 A1 | 5/2012 | Ellis et al. |
| 2012/0116424 A1 | 5/2012 | Lee et al. |
| 2012/0193394 A1 | 8/2012 | Holcomb et al. |
| 2012/0232586 A1* | 9/2012 | Yeh ..................... A61B 17/0057 606/215 |
| 2012/0245629 A1 | 9/2012 | Gross et al. |

(56) References Cited

U.S. PATENT DOCUMENTS

| | | |
|---|---|---|
| 2012/0248171 A1 | 10/2012 | Bailly et al. |
| 2012/0265218 A1 | 10/2012 | Chen et al. |
| 2012/0310259 A1 | 12/2012 | Sorrentino et al. |
| 2012/0330354 A1 | 12/2012 | Kane et al. |
| 2012/0330356 A1 | 12/2012 | Rosenberg |
| 2013/0012961 A1 | 1/2013 | Reeser |
| 2013/0018394 A1 | 1/2013 | Gambale |
| 2013/0186936 A1 | 7/2013 | Shelton, IV |
| 2013/0317524 A1 | 11/2013 | Grigoryants et al. |
| 2014/0257339 A1 | 9/2014 | Levy et al. |
| 2015/0272566 A1 | 10/2015 | Arai et al. |

FOREIGN PATENT DOCUMENTS

| | | |
|---|---|---|
| EP | 1 206 924 A1 | 5/2002 |
| EP | 1 721 575 A2 | 11/2006 |
| EP | 1 759 812 A1 | 3/2007 |
| JP | 5-161655 A | 6/1993 |
| WO | 96/03925 A1 | 2/1996 |
| WO | 01/65997 A2 | 9/2001 |
| WO | 2007/139785 A2 | 12/2007 |
| WO | 2009/100242 A2 | 8/2009 |
| WO | 2011/068533 A1 | 6/2011 |

OTHER PUBLICATIONS

Web page <http://www.covidien.com/silsstitch/pages.aspx> accessed on Mar. 29, 2012 (2 pages).

Web page <http://www.Isisolutions.com/rd180deviceanatomy> accessed on Mar. 29, 2012 (1 page).

Abhishek, et al., 2012, Laparoscopic Umbilical Hernia Repair: Technique Paper, ISRN Minimally Invasive Surgery, pp. 1-4, Article ID 906405.

Nguyen, et al., 2008, Postoperative Pain After Laparoscopic Ventral Hernia Repair: a Prospective Comparison of Clips Versus Tacks, JSLS 12:113-116.

Extended European search report dated Apr. 22, 2015, for European patent application 12859826.5, which application is a regional stage entry of International Patent Application PCT/IB2012/002957, filed Dec. 17, 2012 (5 pages).

International Search Report and Written Opinion dated Feb. 13, 2015, for International Patent Application No. PCT/US2014/001572, filed Mar. 6, 2014 (18 pages).

International Search Report and Written Opinion dated Sep. 26, 2016, for International Patent Application PCT/IB16/00571 with International filing date Apr. 19, 2016 (7 pages).

* cited by examiner

SURGICAL FASTENER DELIVERY AND LOCKING MECHANISM

CROSS-REFERENCE TO RELATED APPLICATION

This application claims priority to, and the benefit of, U.S. Provisional Patent Application Ser. No. 62/151,631, filed Apr. 23, 2015, the contents of which are incorporated by reference.

FIELD OF THE INVENTION

The invention generally relates to devices for hernia mesh fixation.

BACKGROUND

If a person has a hernia, they may suffer from pain, organ dysfunction, bowel obstruction, or other complications. This occurs when an organ protrudes through the wall that normally contains it. Hernias can occur in a number of parts of the body, and occur commonly in the abdomen. For example, the peritoneum that lines the abdomen may push out through a weakened area of the abdominal wall to form a small balloon-like sac. This can allow a loop of intestine or abdominal tissue to push into the sac.

One method of hernia repair involves using a surgical procedure known as laparoscopy to cover the hernia with a prosthetic mesh and fix it in place with fasteners. The fasteners are delivered by a fastening device configured to reach into the abdominal cavity through an incision. A surgeon inserts surgical implements as well as a laparoscope—a small telescope with a camera attached—through small incisions made in the skin, allowing the surgical fastener to be inserted and directed to the hernia. Unfortunately, fastening a hernia mesh via laparoscopic access is fraught with problems. Fasteners do not always fully close properly in the right position and orientation to fasten the mesh properly. If the surgeon realizes this during the procedure, additional fasteners may be deployed. However, an overabundance of foreign objects is thought to contribute greatly to patient pain. If the surgeon does not realize that some of the fasteners have failed to fasten, then the entire procedure may require a do-over.

SUMMARY

The invention provides a fastening device that can be used to deliver a fastener to hernia through a laparoscopic incision and that uses the coordinated operation of two insertion members to stabilize the fastener during closure and locking to ensure that every fastener is fully closed and locked precisely in the intended location before the device releases from the fastener. One of the insertion members includes a pair of biased prongs that are held together when they are pushed into a recess at an end of the fastener. The fastener has a hook at one end and a loop at the other end. The insertion members push the fastener out from the device and through the tissue. A curvature in at least one of the insertion members pushes the hook through the loop all while the prongs are held in the recess in the fastener, thereby stabilizing the fastener with respect to the device (which is typically being held and controlled by the physician). After the hook is locked into the loop, the insertion members are retracted. Upon retraction from the recess, the prongs are pushed aside by the insertion members and/or the fastener, thereby creating a clearance for the closed, locked fastener to pass through as the insertion members are retracted away from closed, locked fastener and back into the device. Thus the device gives the physician the ability to control and stabilize the fastener during the entire closing and locking processes. The physician has direct mechanical contact grasping the fastener, which contact is maintained until after the fastener is closed and locked. Since the device gives the physician the ability to control and stabilize the fastener during the entire closing and locking process, the device will always fully and properly close and lock the fastener in the right position and orientation to fasten the mesh properly. Since the fasteners are always positioned and fastened properly, the physician does not need to deploy additional fasteners to compensate for misfires and much patient pain is avoided. Additionally, since hernia meshes are consistently fastened properly during the procedure, costly and painful do-overs are avoided.

In certain aspects, the invention provides a suturing device having a plurality of fasteners disposed within an applicator section. Each of the plurality of fasteners is formed as a single piece with two terminating ends, where one of the two terminating ends has a hook and the other one of the two terminating ends has a loop. Further, the device includes first and second members movable out of and into the applicator section to deliver, one at a time, each of the fasteners. The first insertion member is configured to engage the hook of one of the fasteners, penetrate the patient's tissue, and carry the hook through the patient's tissue when the first member is moved out of the applicator section. The second insertion member is configured to engage the loop of that fastener, penetrate the patient's tissue, and carry the loop through the patient's tissue when the second member is moved out of the applicator section. One of the insertion members includes a pair of prongs that are positioned together when they are pushed into a recess at an end of the fastener. The insertion members push the fastener out from the device and through the tissue. A curvature in at least one of the insertion members pushes the hook through the loop all while the open-biased prongs are held in the recess in the fastener, thereby stabilizing the fastener with respect to the device (which is typically being held and controlled by the physician). After the hook is locked into the loop, the insertion members are retracted. Upon retraction from the recess, the prongs are separated from one another (e.g., by being dragged over, and pushed apart by, either the closed fastener or the hook insertion member), creating a clearance for the closed, locked fastener to pass through as the insertion members are retracted away from closed, locked fastener and back into the device.

Aspects of the invention provide a device for delivering a plurality of fasteners, one at a time, into tissue of a patient. The device includes a handle including a trigger, a shaft extending from the handle and dimensioned for insertion into a patient's abdomen through an incision in the abdomen, and an applicator section at a distal end of the shaft. The plurality of fasteners are disposed within the applicator section and each of the plurality of fasteners is formed as a single piece with a hook at one end and a loop at the other end. The device includes first and second members operably coupled to the trigger. Activation of the trigger by a user causes (i) the first member to engage the loop of one of the fasteners carry the loop through the patient's tissue, (ii) the second member to engage the hook of that fastener, carry the hook through the tissue, and pass the hook through the loop, thereby locking the fastener into a closed loop in the tissue while the loop remains engaged by the first member, and (iii)

the first and second members to retract into the applicator section leaving the closed fastener in the tissue. The shaft is preferably dimensioned for insertion into the abdomen through a trocar placed in the an incision. Preferably, the first and second members are configured to penetrate a prosthetic mesh and the patient's tissue.

In some embodiments, a distal tip of the first member defines a pair of prongs configured to be inserted into a recess at a distal end of the loop of the fastener. The pair of prongs is held in the recess when inserted into the recess. The distal tip of the first member is configured to define an opening corresponding to the loop while the pair of prongs is held together by the recess. The distal tip of the first member (the pair of prongs) includes an elastic material that biases the pair of prongs into a first configuration (e.g., closed) but allows them to be pushed elastically into a second conformation (e.g., open) to define a gap between the pair of prongs. Retraction of the first member may include removing the pair of prongs from the recess and withdrawing the distal tip of the first member by allowing the hook end of the fastener to pass through the gap between the pair of prongs.

In certain embodiments, at least one of the first and second members has a flexible, pre-shaped portion that moves along a curved path. The flexible portion remains straight when disposed in the shaft and, upon the activation of the trigger, extends from the shaft and moves along the curved path by assuming a curved shape. That one of the first and second members may move along a path that is both straight and curved outside of the shaft.

The first and second insertion members may be operably coupled to the trigger by first and second push rods that each have a distal end engaged with its respective insertion member and a proximal end engaged with a slot wheel in the handle.

In some embodiments, the device is configured to deliver fasteners of different sizes to different penetration depths within the patient's tissue. Optionally, the applicator section is configured to receive a cartridge loaded with the plurality of fasteners. For example, the cartridge may be from a set of cartridges, at least two of the cartridges in the set carrying fasteners of a different size.

DETAILED DESCRIPTION

The invention relates to a new locking concept for use with hernia mesh fasteners. In some prior art devices, the insertion mechanisms are pulled away before the fastener is fastened, raising the specter of risk that an unfastened fastener will be left in tissue. Using a device of the invention as described herein that risk is avoided by holding the loop in place by the loop inserter while the hook is passed thru it. Only once the hook is completely inserted into the loop and the fastener is locked the insertion needles are retracted. In order to accomplish this, a new insertion member with prongs is included in the device. The new insertion member allows for its retraction while the hook of the fastener is position inside the loop.

In certain embodiments, the prongs comprises a superelastic material such as the nickel titanium alloy Nitinol. The prongs may be biased to the closed position but are temporarily deformed to the open position by being retracted back into the delivery device after delivery, the prong being spread open by passing over the delivered fastener or one of the delivery members.

In some embodiments, the prongs define a pair of open-biased prongs that include an elastic material (e.g., Nitinol) defining two flexible prongs which converge at the tip of the insertion member. In the open-biased embodiment, the rest position for the prongs is opened, but a recess on the fastener holds the prongs together during delivery. When withdrawn from the fastener, the prongs spring open to give clearance for the fastener.

In either embodiment, the two prongs can be separate or spaced apart at their tips and can flex laterally, thus creating a gap. When the insertion member is within device, the tip can be inserted into a pocket at one end of the fastener and can push that end into the tissue. While the insertion member is retracted it slides out of the pocket and the prongs separate laterally as a result of sliding on top of the hook inserter or the fastener body.

Figure 1:
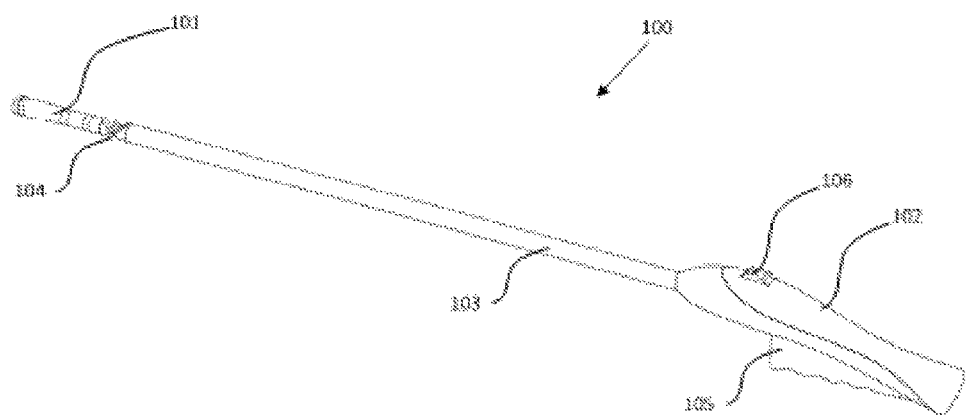
FIG. 1 shows a fastening device for hernia repair.

FIG. 1 shows a fastening device 100 according to certain embodiments. Fastening device 100 is adapted to place and secure at least one fastener inside a tissue during a minimal invasive surgical operation. Fastening device 100 has an applicator section 101 and a handle section 102 connected via shaft 103. Applicator section 101 is adapted to pass through an incision or standard trocar, and to make contact with, and insert a fastener into, the tissue. Because the device is for minimally invasive surgery, the shaft preferably has a length L of at least 15 cm and has a diameter D of less than 1 cm. Applicator section 101 operates as a fastener carrier by being operably connected to shaft 103 (e.g., either one can be partially disposed within the other, they can be manufactured and assembled together, etc.).

Handle section 102 allows a practitioner to control fastener application. Handle section 102 includes trigger 105, which may generally include a lever mechanism. Operation of trigger 105 delivers and fastens a fastener as described below.

Figure 2:
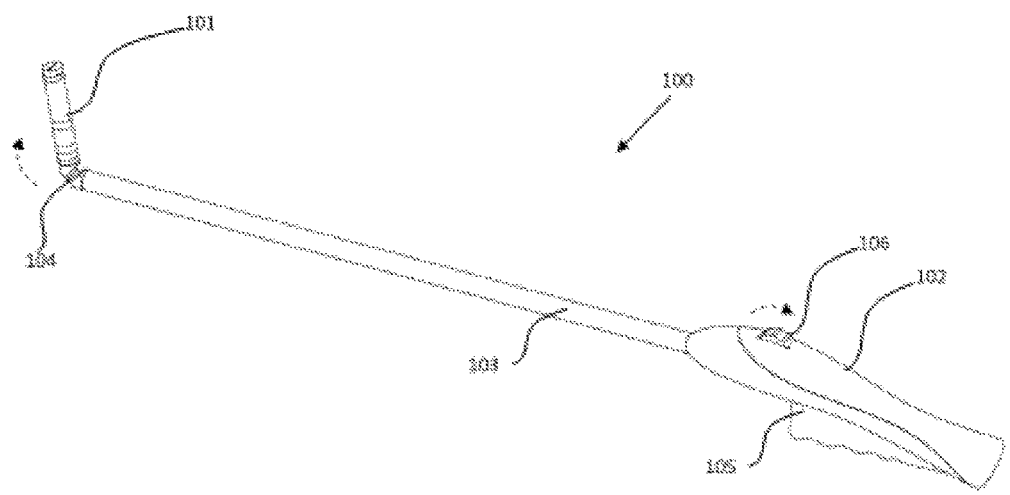
FIG. 2 shows articulation of a shaft of the device.

In certain embodiments, shaft 103 is articulated around an articulation joint 104 in order to place a fastener inside the tissue in a correct angle in respect to the tissue surface FIG. 2 shows articulation of shaft 103. Handle 102 includes articulation knob 106 adapted to control the articulation. Since shaft 103 may be bent at articulation joint 104, a physician may navigate the applicator section 101 to the hernia mesh within the abdomen.

Figure 3:
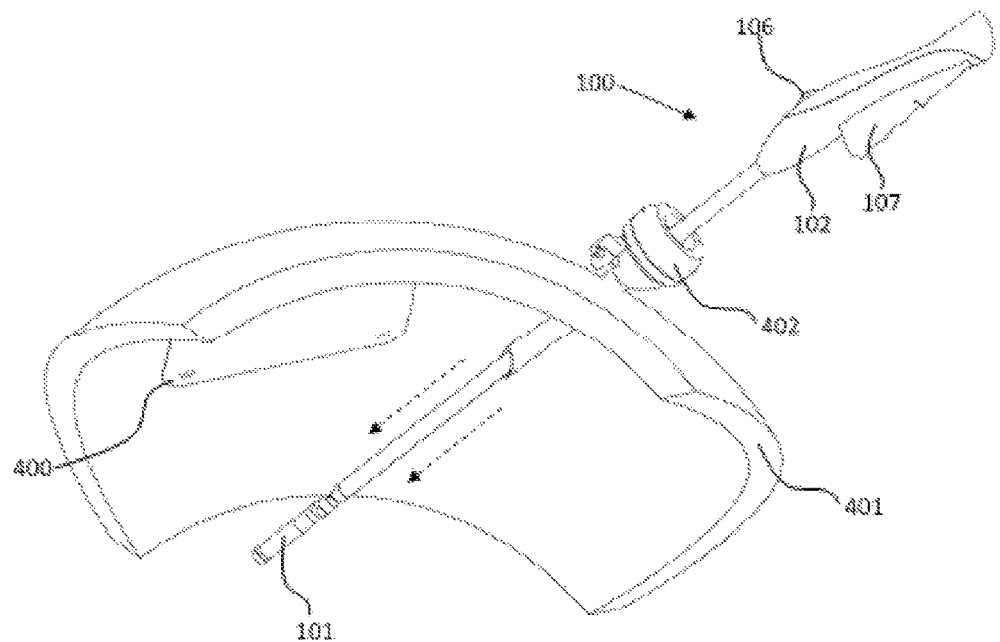
FIG. 3 illustrates navigation of the applicator section to the hernia mesh.

FIG. 3 illustrates navigation of the applicator section 101 to the hernia mesh within the abdomen. Device 100 is used for securing a hernia mesh 400 to the innermost layer of abdominal wall 401 during laparoscopic hernia repair surgery. In general, the outermost layer of the abdominal wall is the skin, followed by two layers of fibrous connective tissue (the campers fascia then the Scarpas fascia), three layers of muscle (the external oblique muscle, the internal oblique muscle, and the transverse abdominal muscle), a layer of fat (the preperitoneal fat), and then the peritoneum—a membrane that surrounds the abdominal cavity. Methods include inserting a distal portion of fastening device 100 into a patient's abdominal cavity through a trocar 402 or through an incision.

Figure 4:
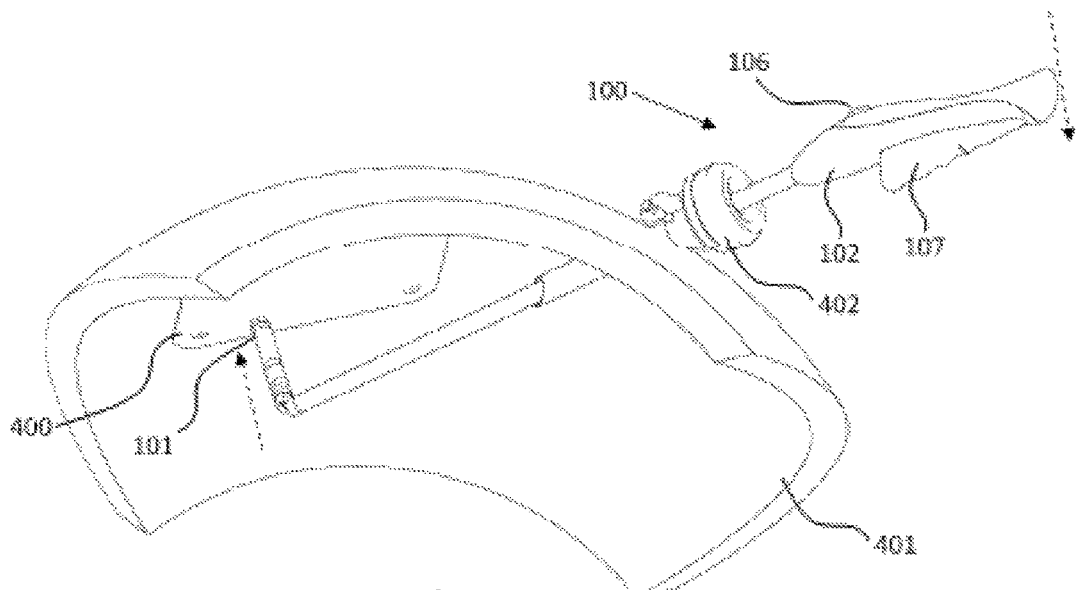
FIG. 4 shows articulation of the applicator section.

FIG. 4 shows articulation of the applicator section 101 via articulation knob 106. Distal tip 301 is pressed against hernia mesh 400 and a single fastener is delivered through the tissue and hernia mesh 400 and secured in place by pressing lever 107 on handle 102. The device 100 is removed from the abdomen through the surgical incision. The device 100 operates with one or a plurality of pre-formed sutures formed to interoperate with mechanisms of the applicator section 101.

Figure 5:
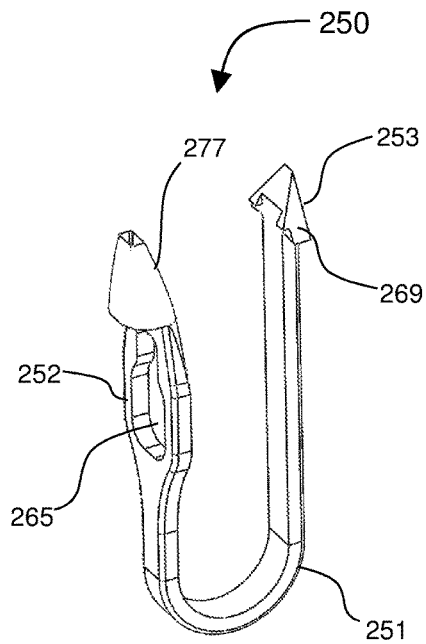
FIG. 5 shows a fastener for use with a device of the invention.

FIG. 5 shows a fastener 250. Preferably, the fastener 250 is pre-formed to have substantially the shape shown in FIG. 5. The fastener 250 includes an extended body 251. A first end 253 of the fastener includes a hook 269. The second end 252 of the fastener includes a loop 265 as well as a sloped portion 277 that can be driven through soft tissue. The hook end may be pushed through the loop 265.

Figure 6:
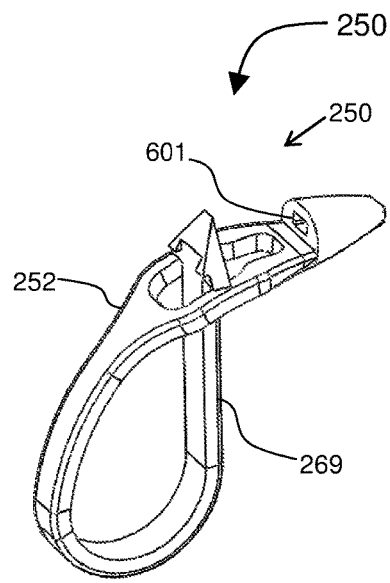
FIG. 6 shows the fastener 250 as it is being closed.

FIG. 6 shows the fastener 250 as it is being closed and the hook 269 is being passed through the loop 265. After the fastener is closed, it may further be locked closed by drawing the neck of the hook 269 up into the narrowest portion of the loop 265. Additionally, FIG. 6 shows a recess 601 on a back surface of insertion slope 277.

Figure 7:
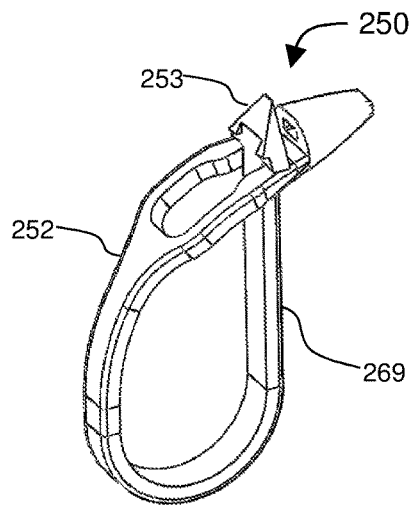
FIG. 7 shows the fastener 250 in a locked configuration.

FIG. 7 shows the fastener 250 in a locked configuration. The fastener 250 includes insertion slope 277 and at least one barb 269 that are dimensioned to operate with the insertion members of device 100. First member 253 includes a hook and second member 252 includes a loop. The fastener 250 is configured to be carried and delivered by the applicator section 101 of device 100.

Figure 8:
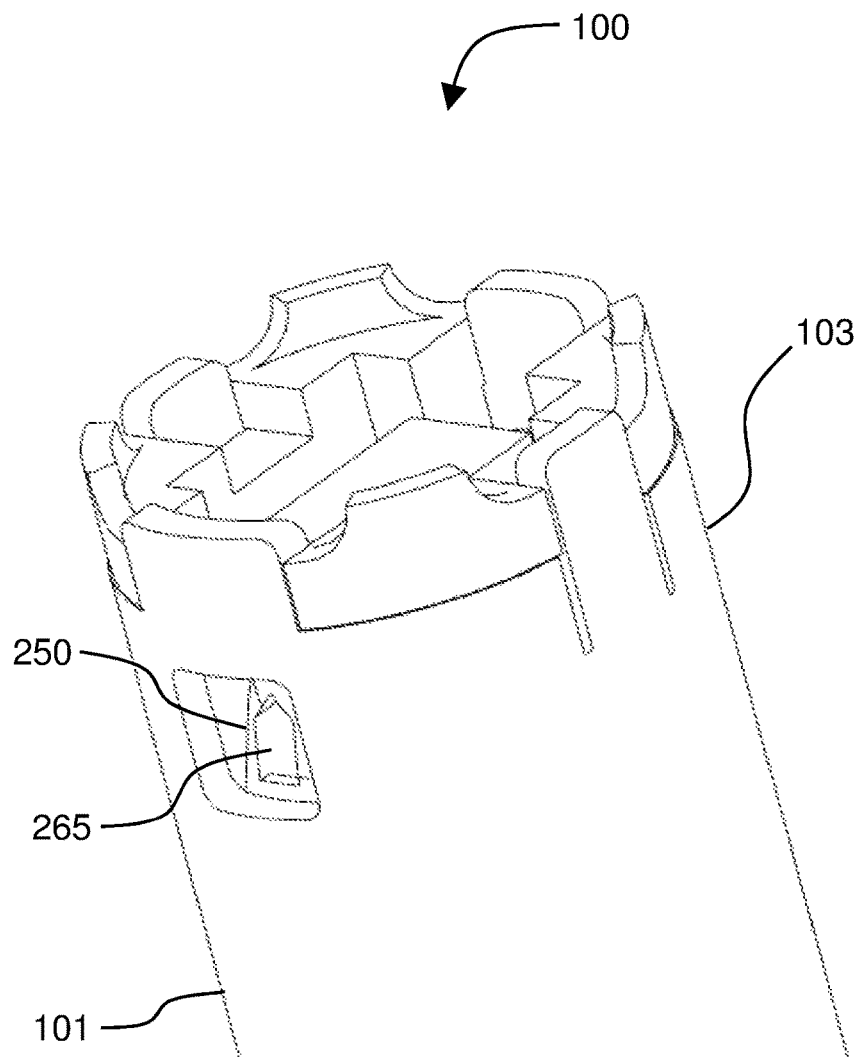
FIG. 8 gives a close-up view of the applicator section of the device.

FIG. 8 gives a close-up view of the applicator section 101 of device 100. Just visible within the applicator section 101 is the portion of fastener 250 where the loop 265 is located. This is the disposition of the fastener 250 when the distal end of the shaft 103 is pressed against the tissue (e.g., FIG. 4). Activation of the trigger 105 causes the insertion members to collect and deliver the fastener 250.

Figure 9:
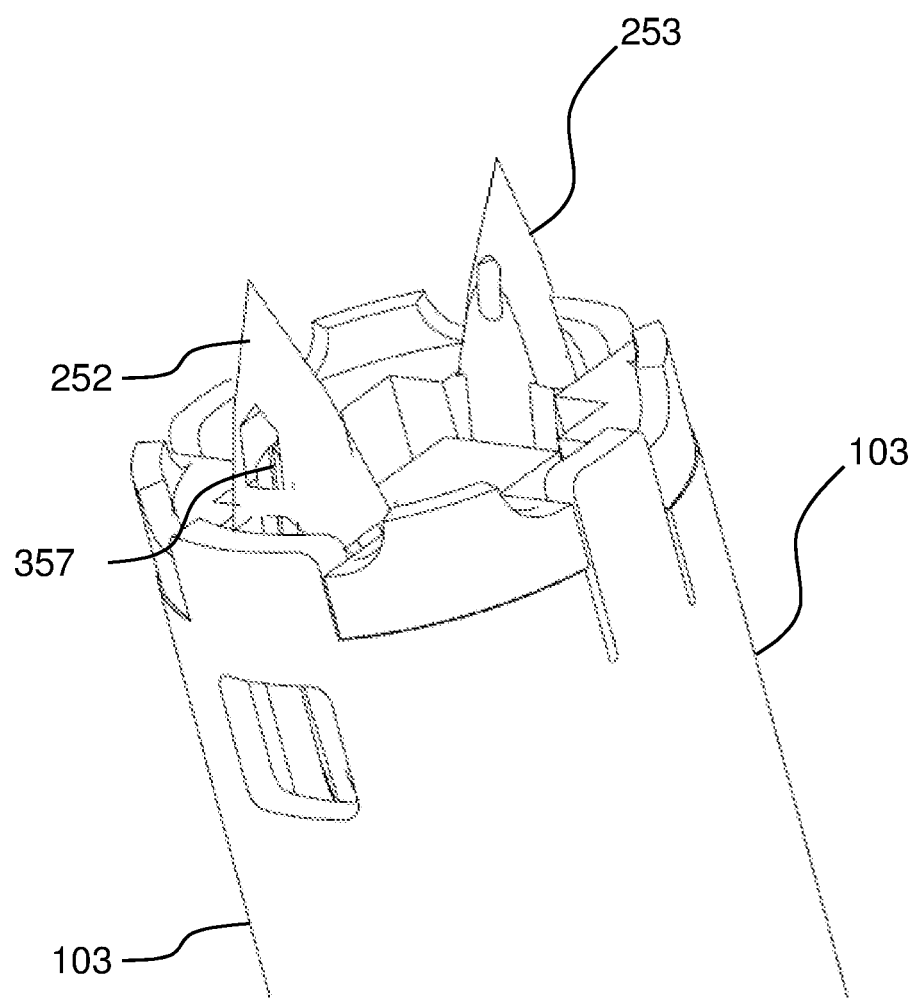
FIG. 9 shows the loop insertion member delivering the fastener.

FIG. 9 shows the loop insertion member 357 collecting and delivering the second end 252 of the fastener 250. Specifically, upon activation of the trigger, the hook insertion member 352 is collecting and delivering the first end 253 of the fastener 250 to engage the hook of that fastener and carry the hook through the tissue. The loop insertion member 357 engages the second end of the fastener 250, thereby engaging the loop 265 of the fastener 250 to carry the loop through the patient's tissue. The loop insertion member 257 includes a pair of elastic prongs.

Figure 10:
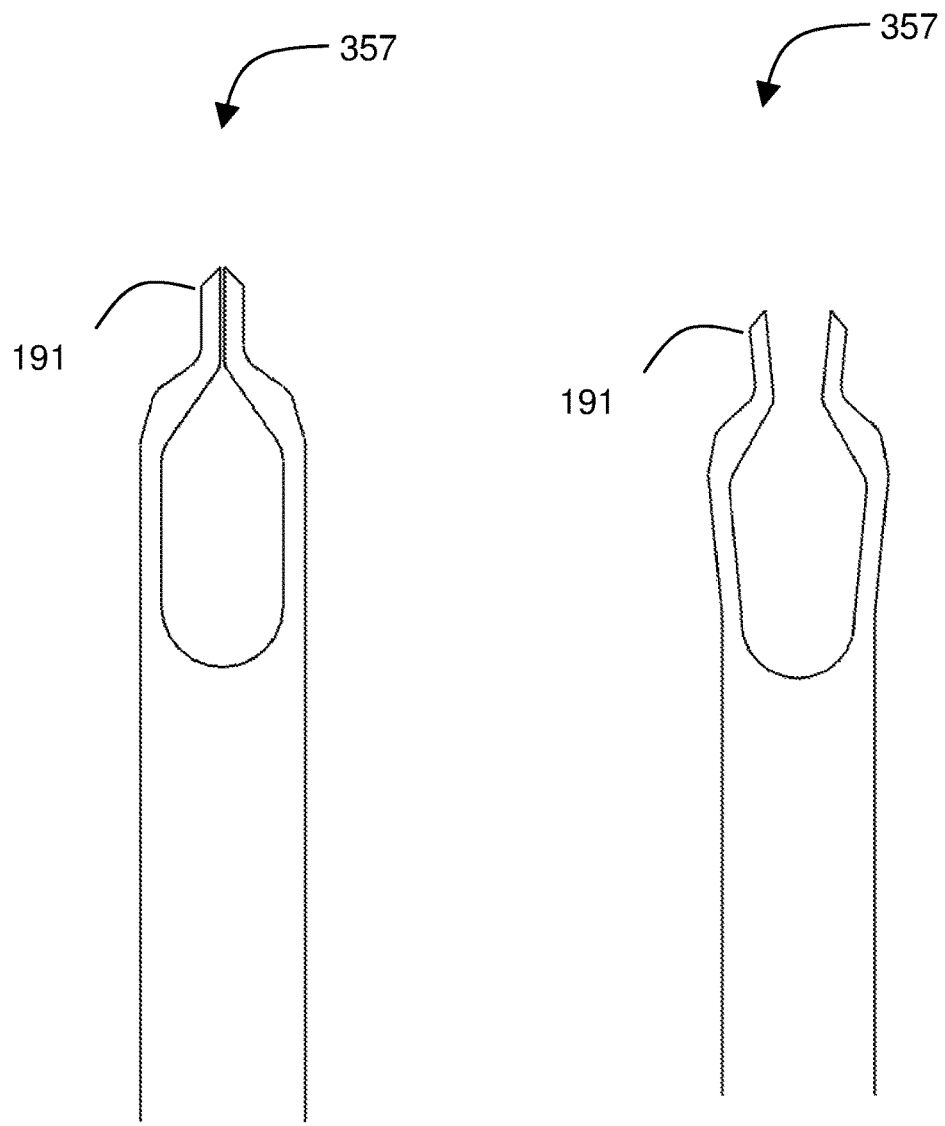
FIG. 10 gives two views of the loop insertion member.

FIG. 10 gives two views of the loop insertion member 357. The view on the right shows the elastic prongs 191 in the open conformation. The view on the left illustrates the conformation that the prongs assume when they are captured by recess 601 (visible in FIG. 6).

Figure 11:
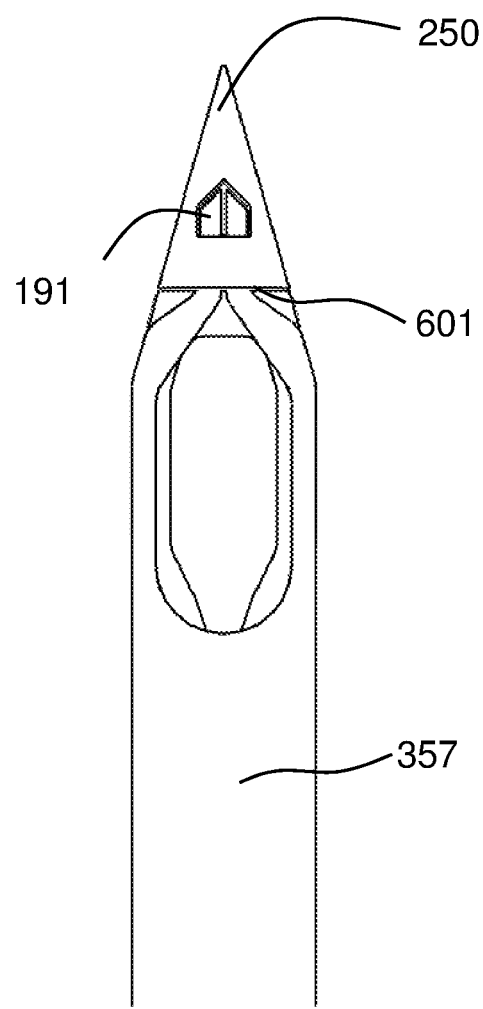
FIG. 11 shows the prongs of insertion member captured by a recess on the fastener.

FIG. 11 shows the prongs of insertion member 357 captured by recess 601 on the loop end of a fastener 250. In operation of device 100, the suture 250 is collected by the hook inserter 352 and the loop inserter 357.

Figure 12:
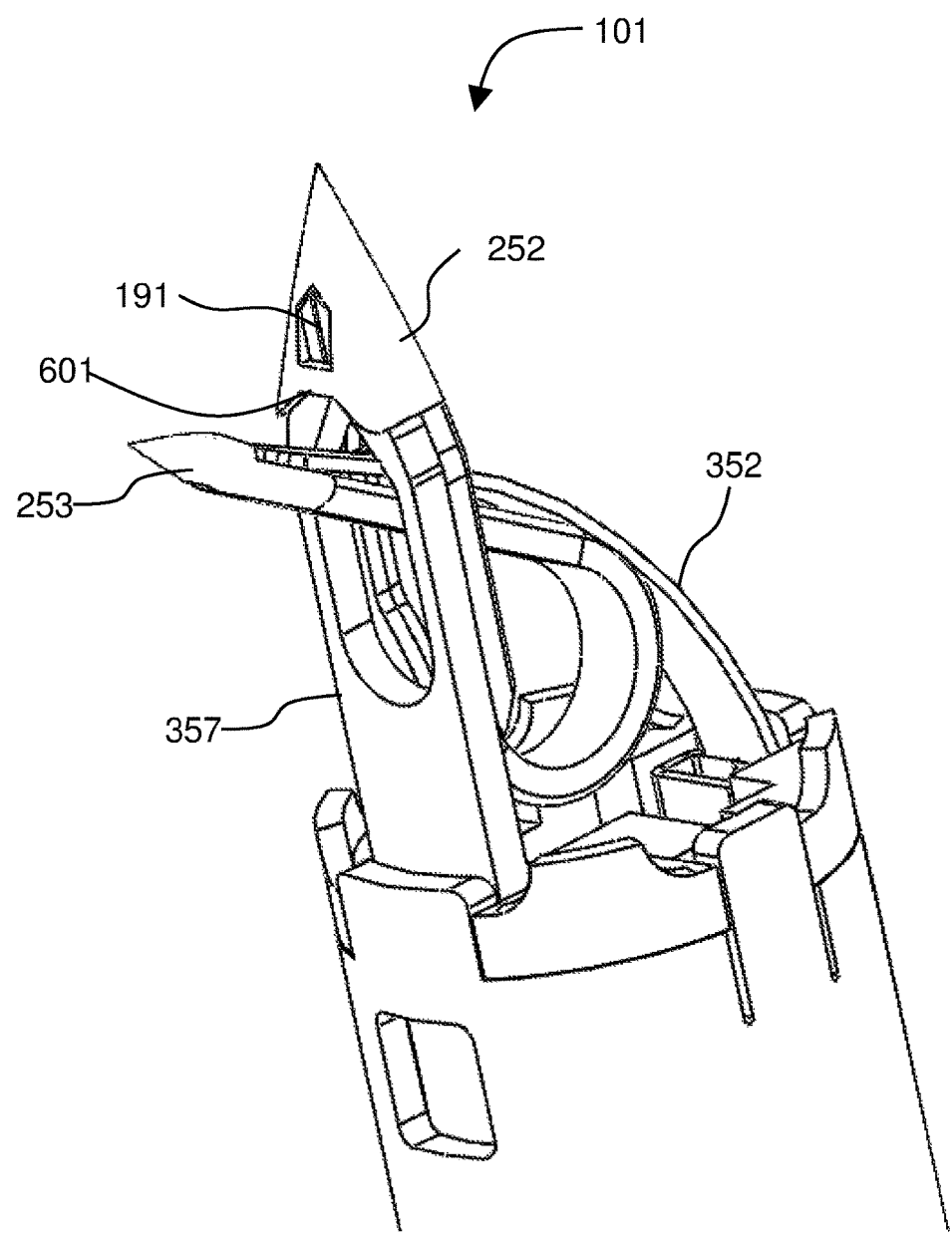
FIG. 12 shows applicator section closing the fastener.

FIG. 12 shows applicator section 101 operating to close the fastener 250 within tissue. The loop is deployed straight inside the tissue and the hook is inserted into the loop. The hook 269 passes through the loop 265 locking the fastener into a closed loop in the tissue while the loop remains engaged by the first member. The two insertion members stabilize the fastener 250 during closure and locking to ensure that every fastener 250 is fully closed and locked precisely in the intended location before the device releases from the fastener. The elastic prongs 191 are disposed together in recess 601. As shown in FIG. 12, the insertion members have pushed the fastener 250 out from the device and through the tissue. A curvature in the hook insertion member 352 pushes the hook 253 through the loop all while the prongs 191 are held in the recess 601 in the fastener 250, thereby stabilizing the fastener 250 with respect to the device 100 while the device is being held and controlled by the physician. After the hook is locked into the loop, the insertion members are retracted.

Figure 13:
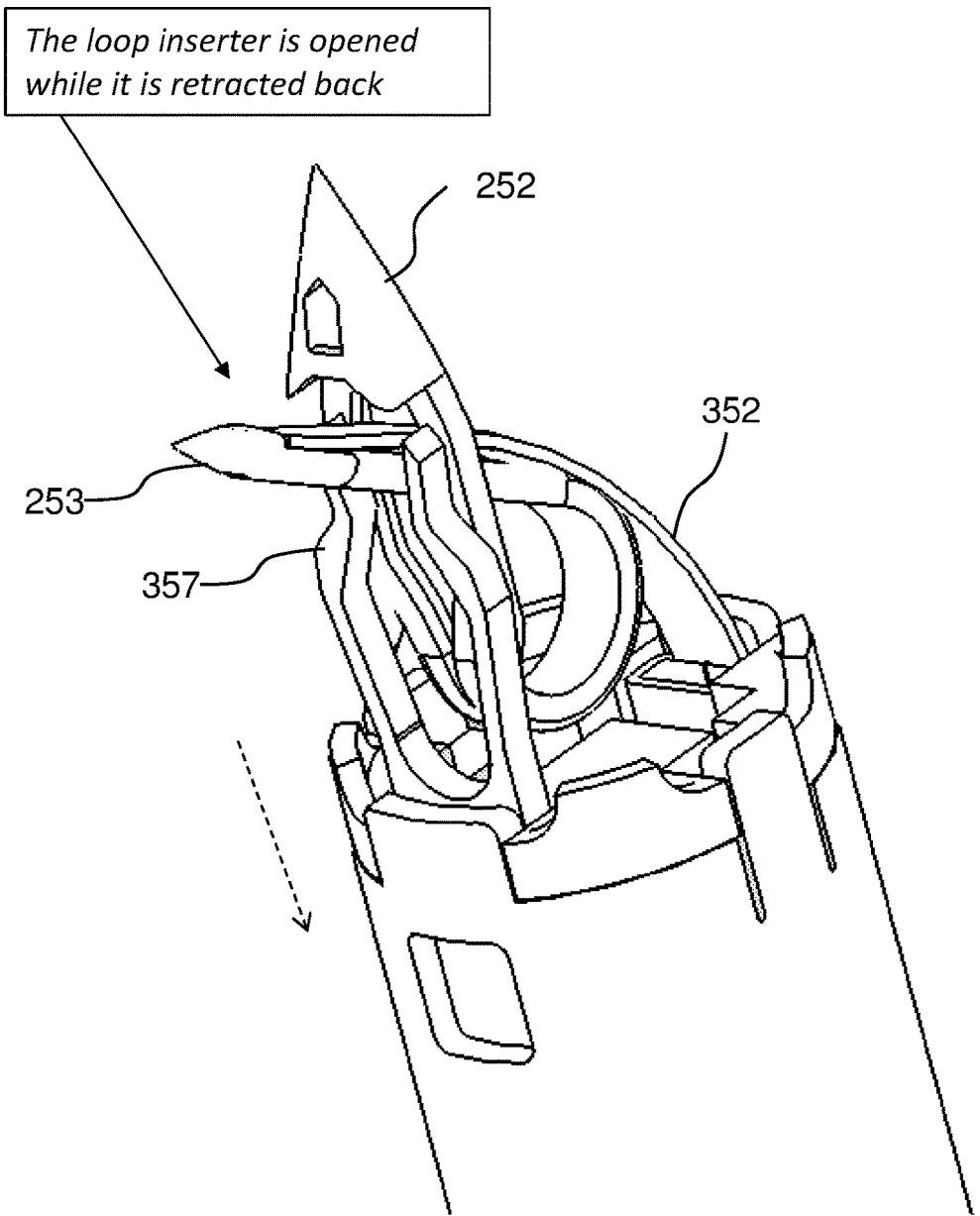
FIG. 13 illustrates retraction of the insertion members.

FIG. 13 illustrates retraction of the insertion members. The loop inserter is retracted back, and the prongs 191 flex laterally while they slides over the hook insertion member 352.

Figure 14:
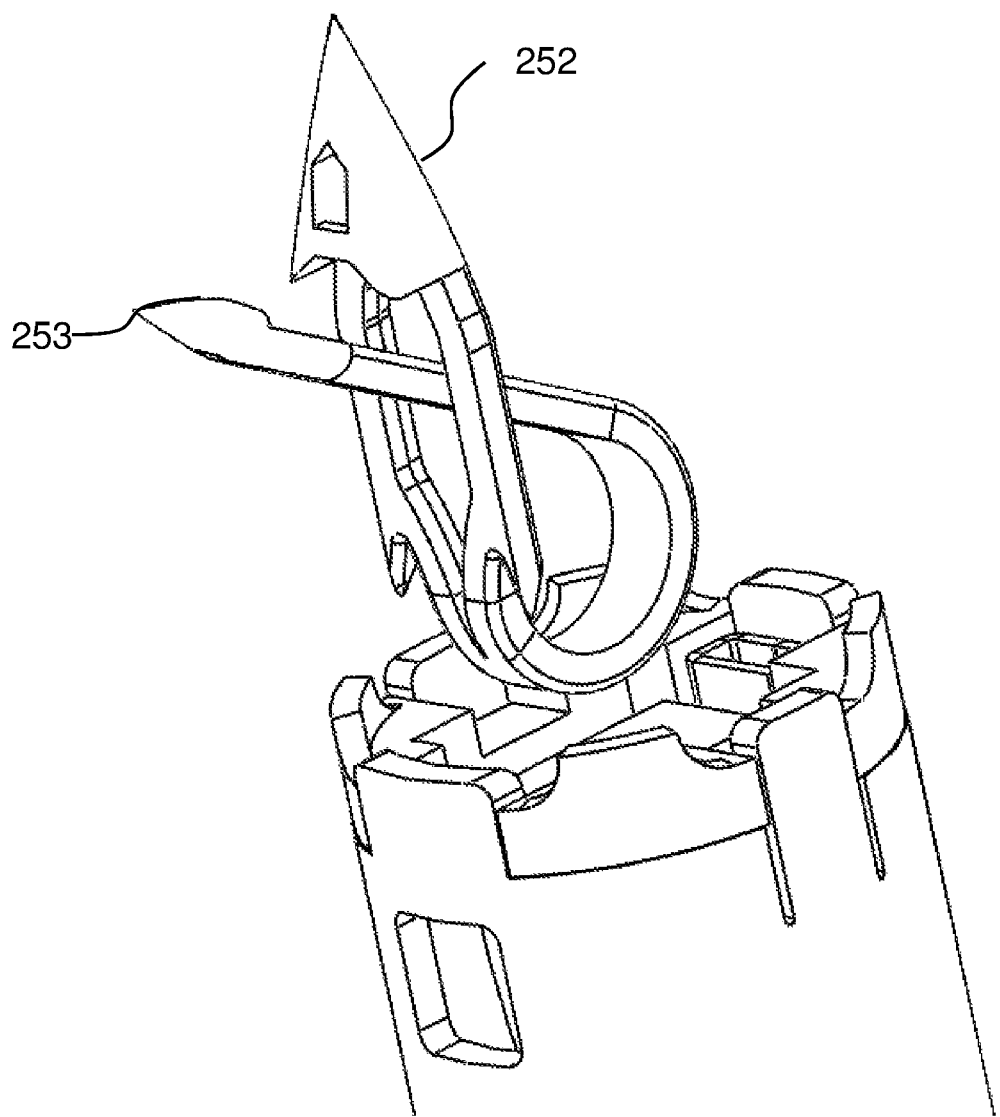
FIG. 14 shows the fully retracted insertion members.

FIG. 14 shows the loop inserter and the hook inserter fully retracted, leaving the fastener 150 locked inside the tissue.

In certain embodiments, a reticulation of the distal end of fastening device 100 allows the distal tip to be rotated around its longitudinal axis. This can allow the application of fasteners in various orientation in respect to said fastening device 100.

Figure 15:
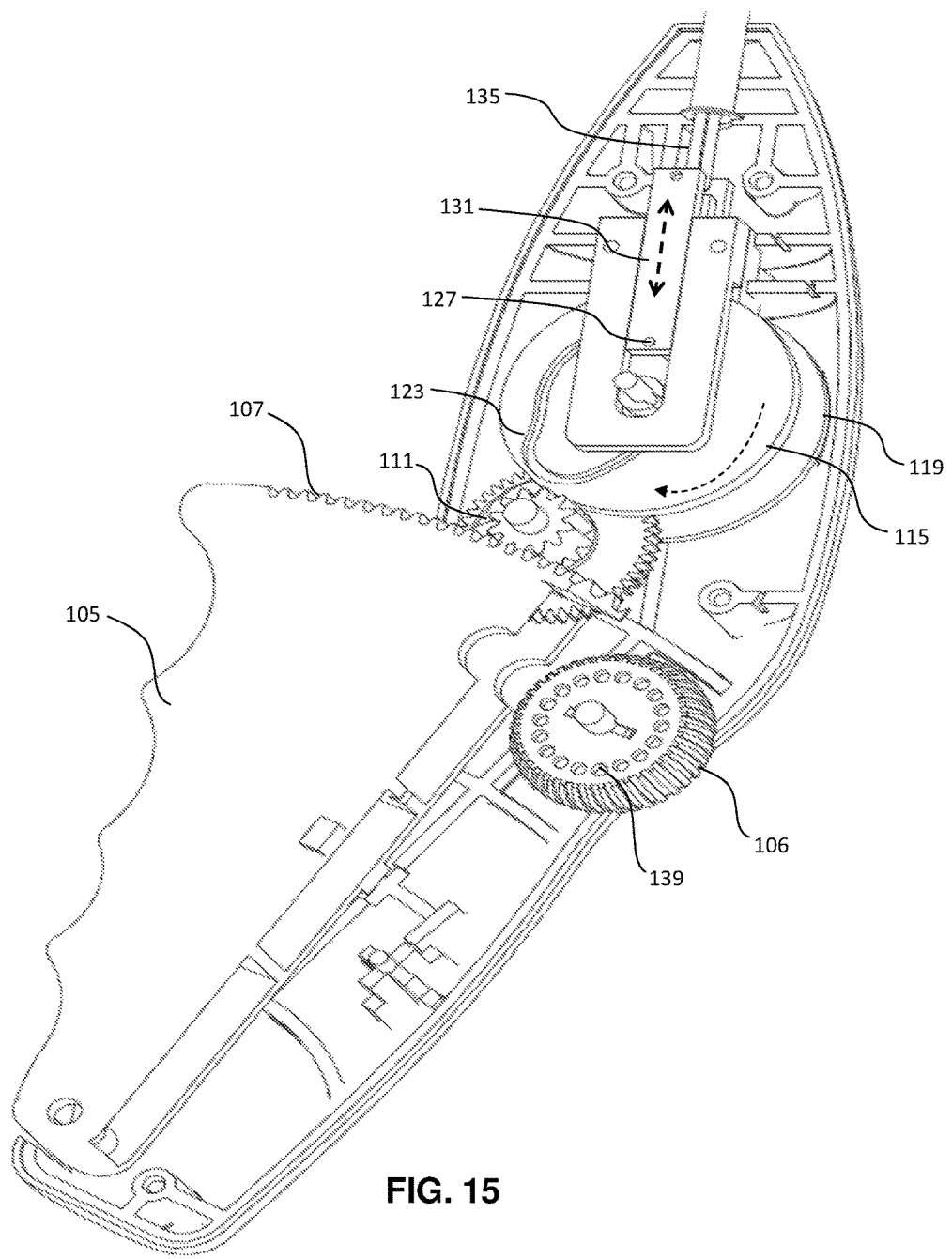
FIG. 15 shows mechanical components in the handle of the fastening device.

FIG. 15 shows components of a handle of a fastening device. As can be seen in FIG. 15, one or more of push rod 135 are linked to one or more of translator bar 131. Translator bar 131 has a pin 127 fixed into a slot 123 of slot wheel 115. As shown in FIG. 15, applicator 100 includes a second slot wheel 119. Additional slot wheels may be included. The rotation of the slot wheel is driven through gear mechanism 111 by a geared face 107 of trigger 105.

By the relationship of these parts, when trigger 105 is squeezed, each of the slot wheels rotate. Because each slot (e.g., slot 123) is irregularly shaped (e.g., not a circle concentric with slot wheel 115), the corresponding translator bar translates independently relative to handle 102 and with acceleration defined by the disposition of the slot. The independent translation of translator bar 131 causes the independent translation of push rod 135 which cause the independent action of hook insertion member 352 and loop insertion member 357, as described above.

In certain embodiments, the series of coordinated motions of the insertion needles, and the delivery of a fastener, is operated and coordinated electronically. For example, applicator device 100 can include servomotors operably connected to a governing circuit and/or chip. A motor can drive the slot wheels. Or, motors can drive each push rod as governed by a chip executing instructions provided, for example, by a tangible, non-transitory computer memory such as, for example, a field-programmable gate array or a disc drive.

Figure 16:
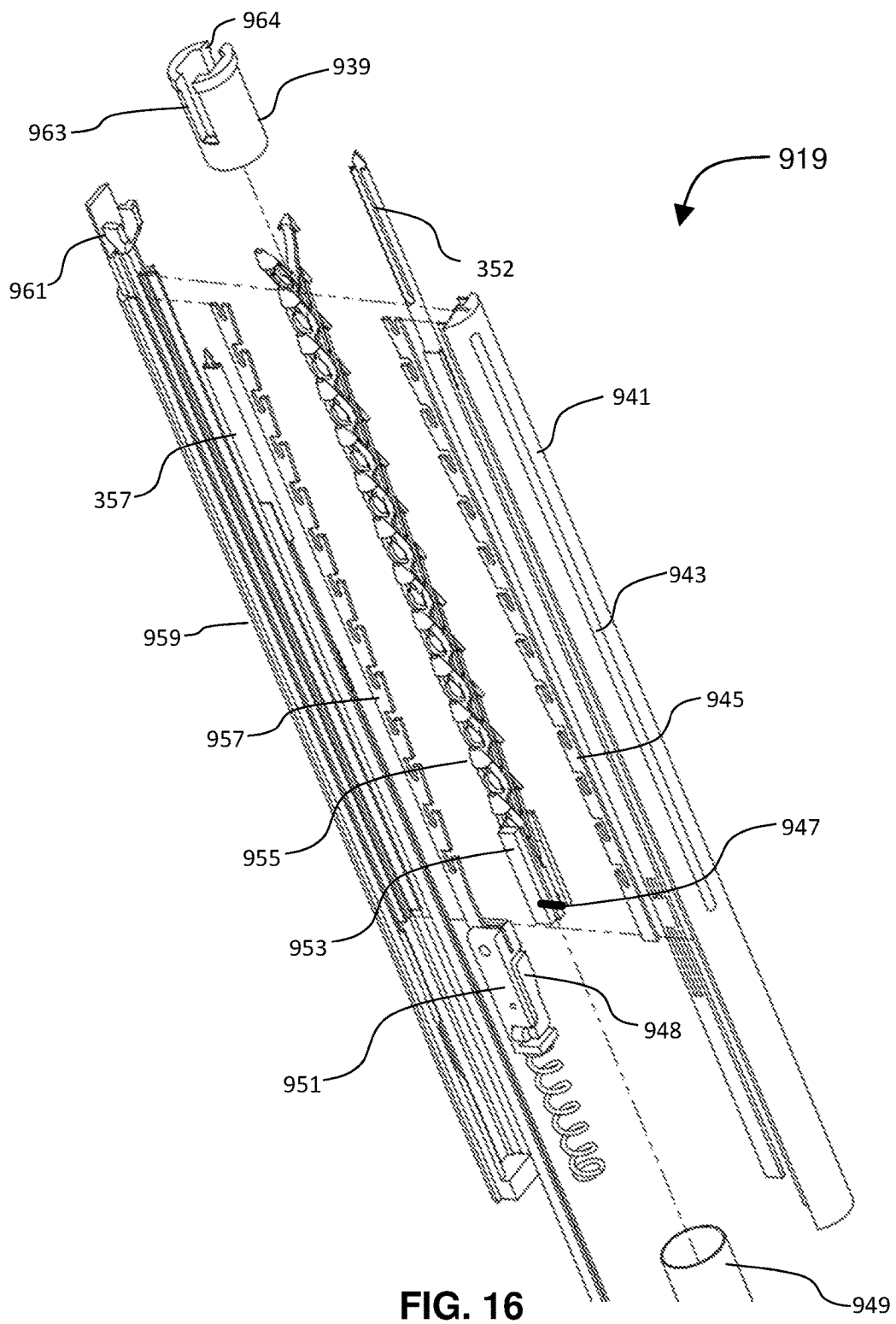
FIG. 16 shows the structure of the fastener feeder.

FIG. 16 shows the structure of the fastener feeder 919. Hook insertion member 352 lies under front feeder cover 941, which includes marker slot 943. Front cover 941 covers hold comb 945. Fastener stack 955 includes a plurality of the fastener 250 extending from fastener support slide 953, which also includes marker pin 947. Front cover 941 and back cover 959 covering and holding the fastener stack 955 and the fastener support 953, said front and back cover can be at least partially, substantially, or entirely encapsulated within the shaft cover 949 and terminate at shaft cap 939. Comb driver assembly 951 with comb driver hook 948 operates drive comb 957, as described below. Fastener feeder 919 includes loop insertion member 357 disposed near fastener spreader 961. Shaft cap 939 includes a loop collection slot 963 and a hook collection slot 964. Fastener feeder 919 functions to deliver one the fastener 250 from fastener stack 955 per operation of device 100.

Figure 17:
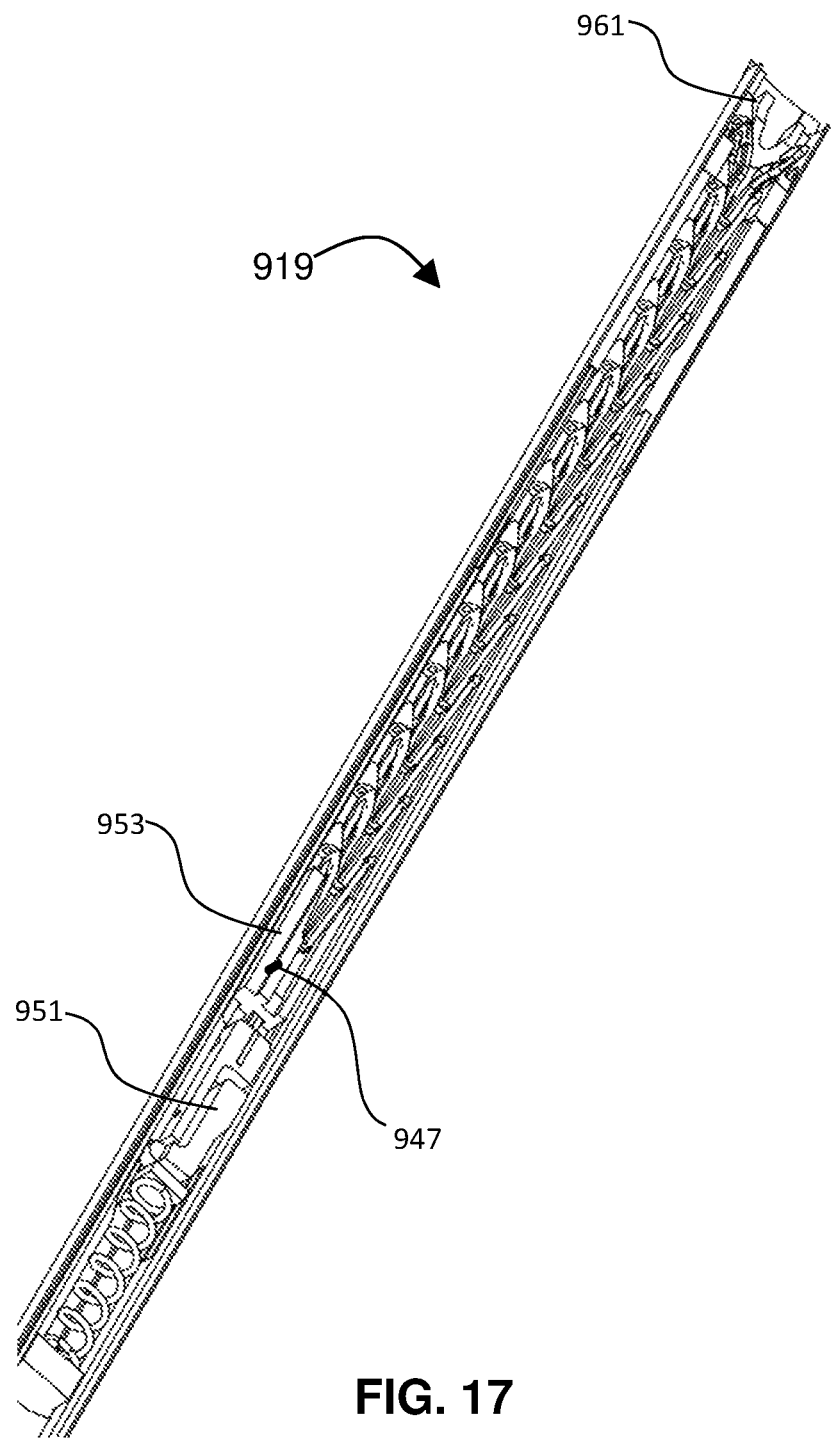
FIG. 17 illustrates an assembled fastener feeder mechanism.

FIG. 17 illustrates an assembled fastener feeder 919. In operation, the comb driver assembly 951 first generates a single up and down stroke of the back drive comb at the end of each application cycle. As a response to the stroke, the entire fastener stack 955 is pushed forward by the drive comb 957. During this process the hold comb 945 (not shown) prevents a downward movement of the pre-formed fasteners 250 in fastener stack 955. Once the fasteners stack 955 is pushed upward (e.g., forward), the last the fastener 250 is spread by the fastener spreader 961 and is positioned at the collection slots 963 and 964, ready to be collected by the insertion needles 352 and 357 during the next application cycle. Each the fastener 250 supports the next the fastener 250 and prevents the lateral movement of its middle while it is pushed by drive comb 957. The last the fastener 250 is supported by the fastener support slide 953. Fastener support slide 953 is pushed by the drive comb 957 together with the fasteners. A marker pin 947 may protrudes to the outer surface of the shaft, through the marker slots at the feeder covers 941, to indicate to the surgeon how many fasteners remains in the device.

Figure 18:
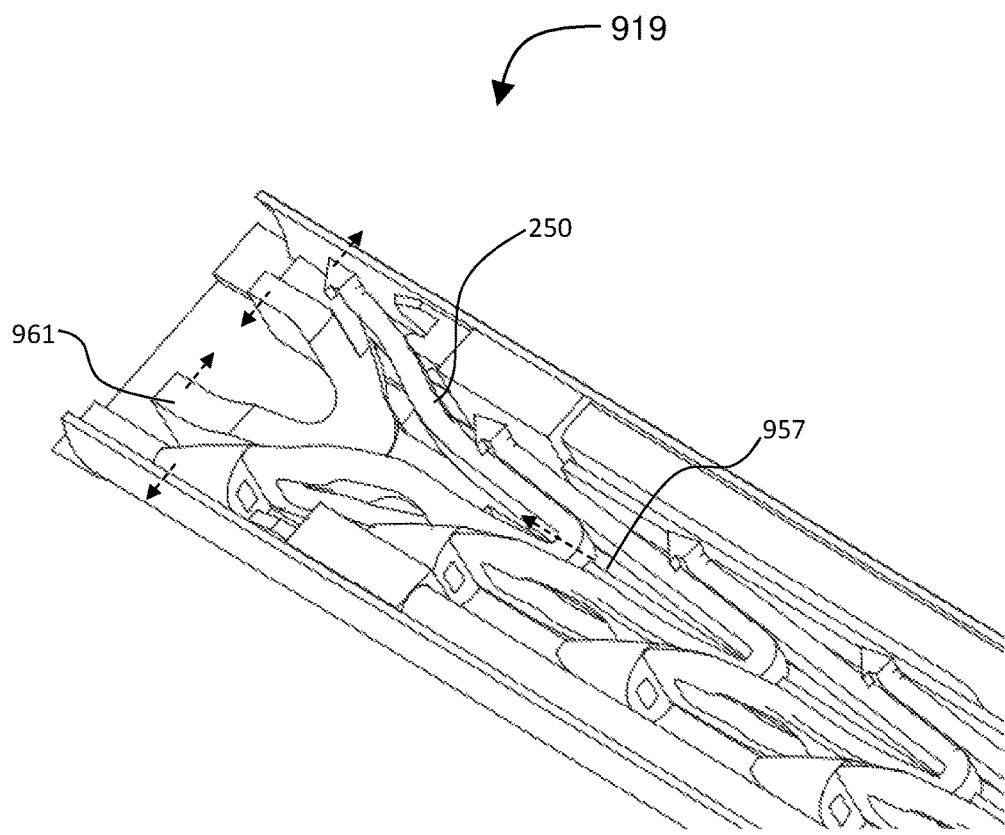
FIG. 18 shows the positioning of a fastener in the fastener feeder.

FIG. 18 shows the positioning of a fastener 250 in fastener feeder 919. The arms of spreader 961 are flexible and can flex toward the center of the shaft in order to allow the ends of the fastener 250 to exit from the device. Spreader 961 also provides resistance in order to allow the integration between needle and the fastener 250 and hold the last the fastener 250 in place before its application. The last the fastener 250 is pushed forward against the spreader 961 by the drive comb 957. As a result, the ends of the fastener 250 are spread into the collection slots 963 and 964 from which they are collected by the insertion needles during the insertion process. The bottom side of the spreader 961 in sloped in order to allow the extraction of the fastener 250 once it was collected by the insertion needles.

FIGS. 19-23 show the advancement of a the fastener 250 through fastener feeder 919. FIGS. 19-23 are cross-sections of a distal end of fastener feeder 919 and they depict a loading of a new the fastener 250 into the collection slots 963 and 964 once a the fastener 250 is applied.

Figure 19:
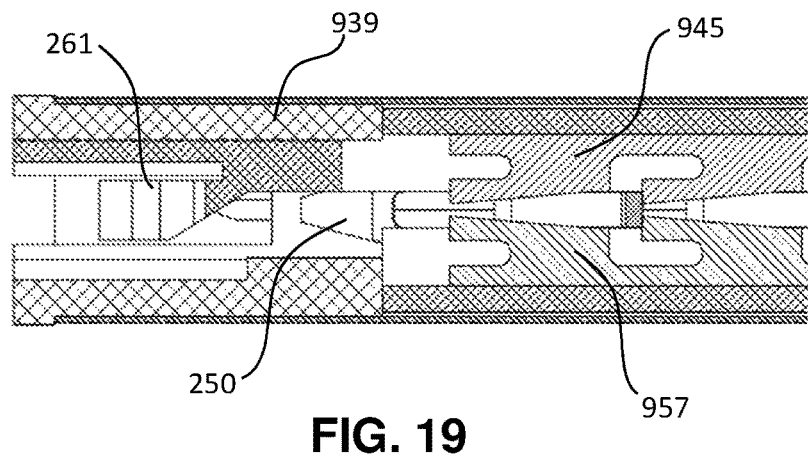
FIG. 19 shows shaft cap in an end the shaft.

FIG. 19 shows shaft cap 939 in an end of shaft cover 949 with fastener spreader 961 therein. In the illustrated embodiment, fastener feeder 919 provides a fastener carrier operably connected to cover 949 of shaft 103. In a related embodiment (not illustrated), front cover 941 and back cover 959 provide at least part of an outer surface of the device and are operably connected to a portion of shaft 103 by a suitable means such as adhesive, threading, press-fit, co-molding, heat staking, etc. Also visible is the fastener 250, being controlled by drive comb 957 and hold comb 945. In an initial stage in FIG. 19, after the first the fastener 250 is collected and inserted into the tissue, the next the fastener 250 is placed below the collection slots 963 and 964.

Figure 20:
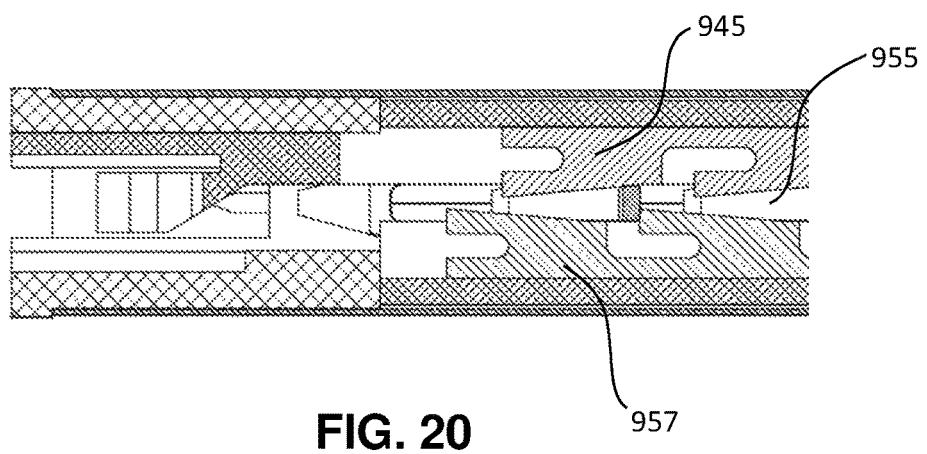
FIG. 20 shows retraction of the drive comb.

FIG. 20 shows retraction of the drive comb 957 while the hold comb 945 is holding the fastener stack 955 in place. The teeth of the drive comb 957 are bent while they are climbing over the fastener stack 955.

Figure 21:
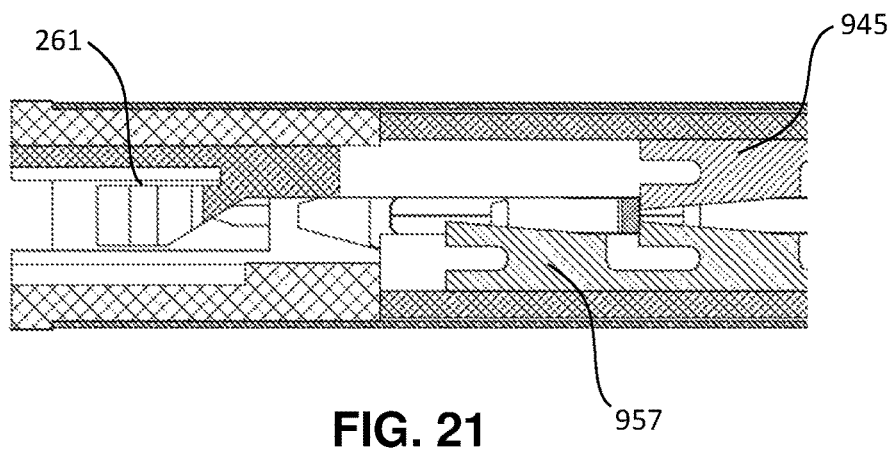
FIG. 21 shows the drive comb engaged with the preformed fasteners.

FIG. 21 shows drive comb 957 engaged with bottom section of the pre-formed fasteners in fastener stack 955.

Figure 22:
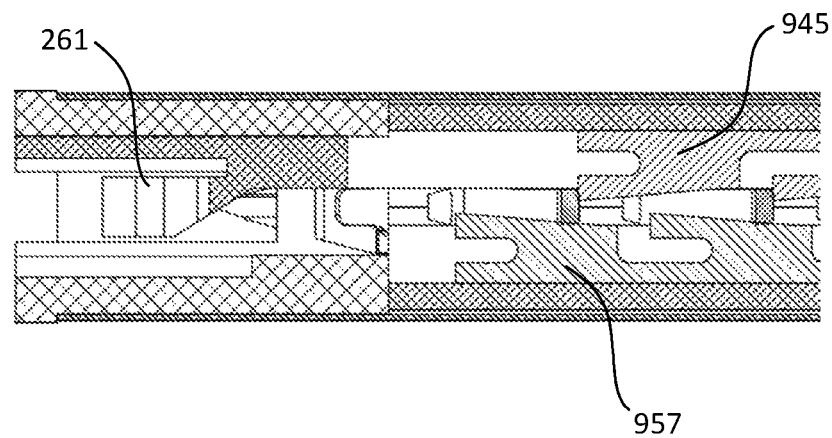
FIG. 22 shows the drive comb pushing one of the preformed fasteners.

FIG. 22 shows drive comb 957 pushing one of pre-formed fasteners 250 forward and toward the spreader 961 while climbing over the teeth of the hold comb 945 (which are bent during the process).

Figure 23:
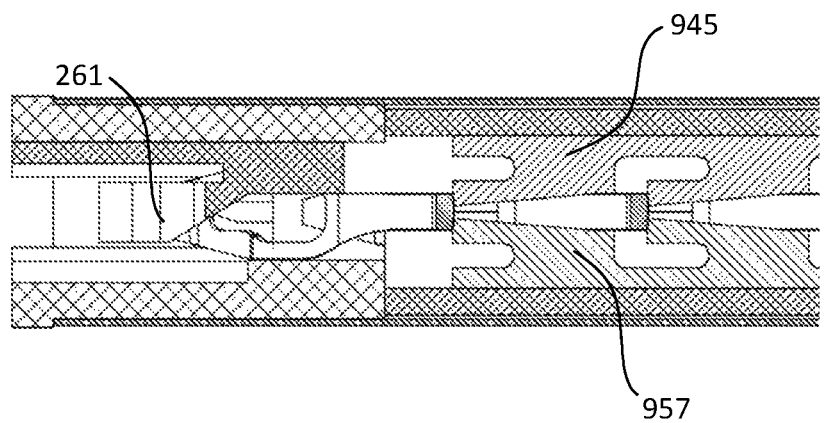
FIG. 23 shows the next the fastener positioned at the collection slots.

FIG. 23 shows the next the fastener 250 positioned at the collection slots 963 and 964 and is ready to be collected by the insertion needles 352 and 357.

FIGS. 24-28 depict the operation of the comb driver mechanism of fastener feeder 919.

Figure 24:
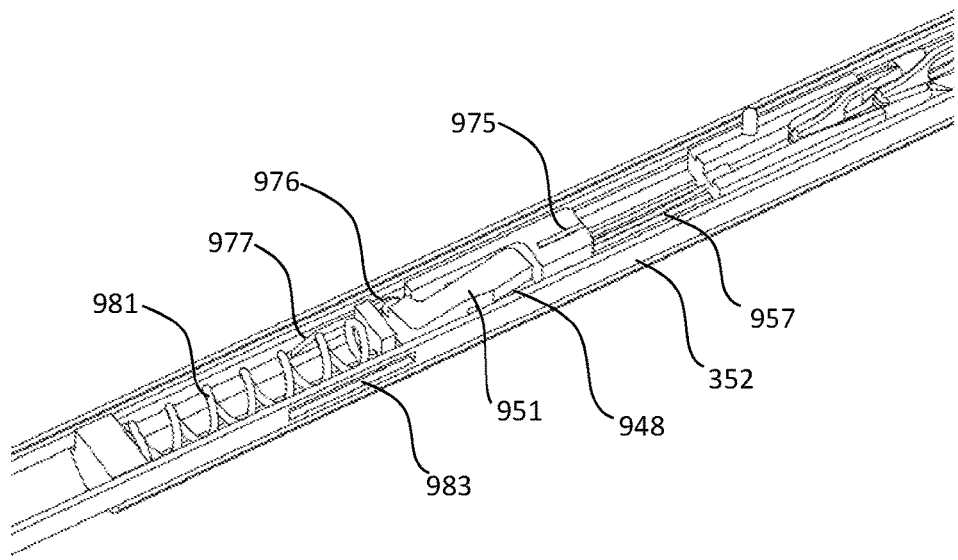
FIG. 24 shows the comb driver assembly.

FIG. 24 shows comb driver assembly 951 providing a connection between comb driver hook 948 plus comb driver slide 975 and drive comb 957. Release slope 977 and release bulge 976 release the comb driver hook from the hook insertion member. Comb driver spring 981 can be seen by hook slot 983. The comb driver hook 948 is connected to the comb driver slide 975 by a flexible pin, allowing its rotation. FIG. 24 shows an initial stage, in which hook inserting needle 352 is positioned backward.

Figure 25:
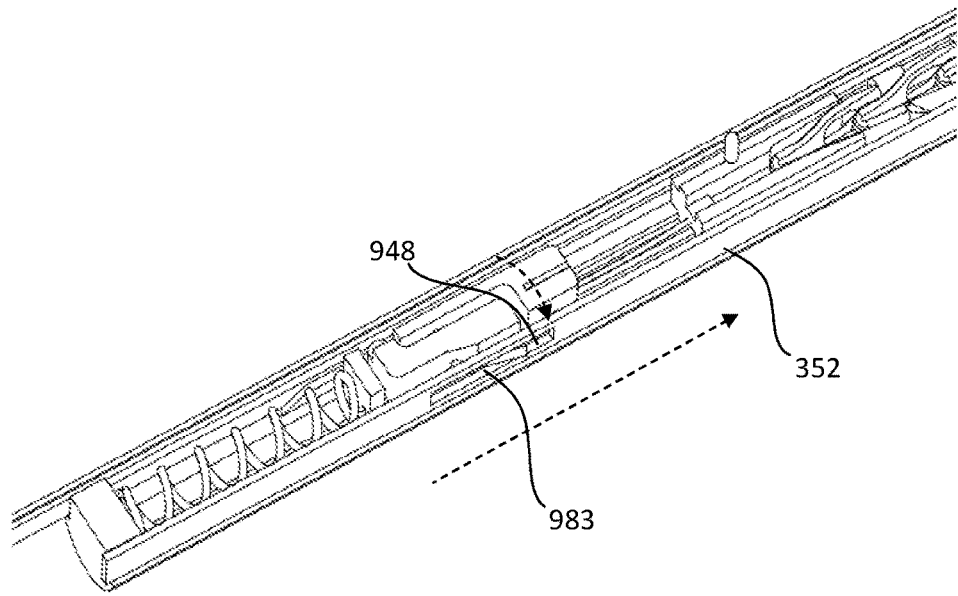
FIG. 25 shows hook engagement.

FIG. 25 shows hook engagement. Once an application cycle starts, hook insertion member 352 moves forward. Once the hook slot 983 is positioned in front of the comb driver hook 948, comb driver hook 948 springs into hook slot 983.

Figure 26:
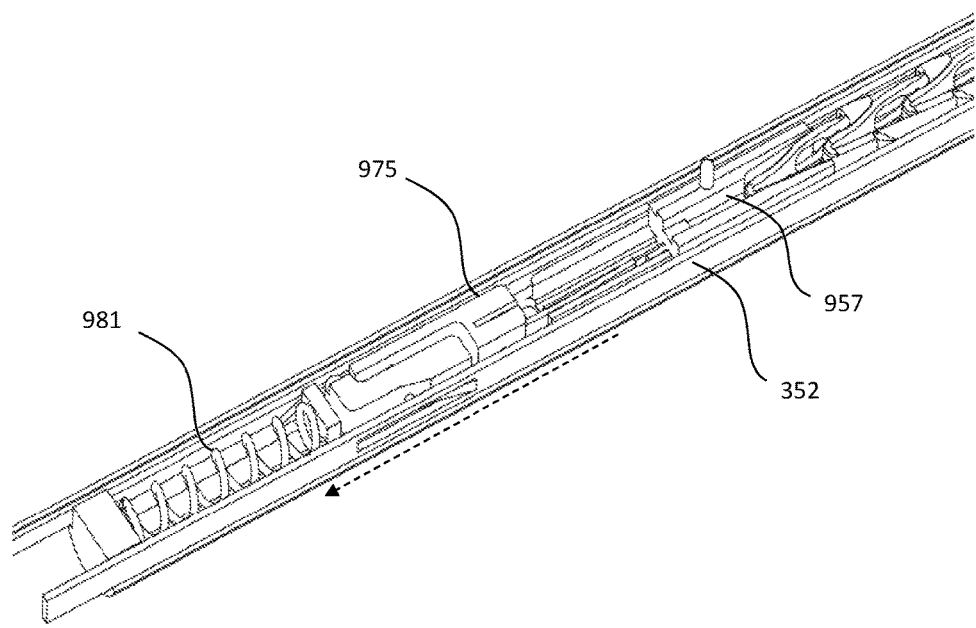
FIG. 26 depicts a pulling back step.

FIG. 26 depicts a pulling back stage. At the final stage of the application cycle, the hook insertion member 352 moves back while pulling the back the comb driver slide 975 and the drive comb 957 while pressing the comb driver spring 981. During this movement the comb teeth are engaged with pre-formed fasteners 250.

Figure 27:
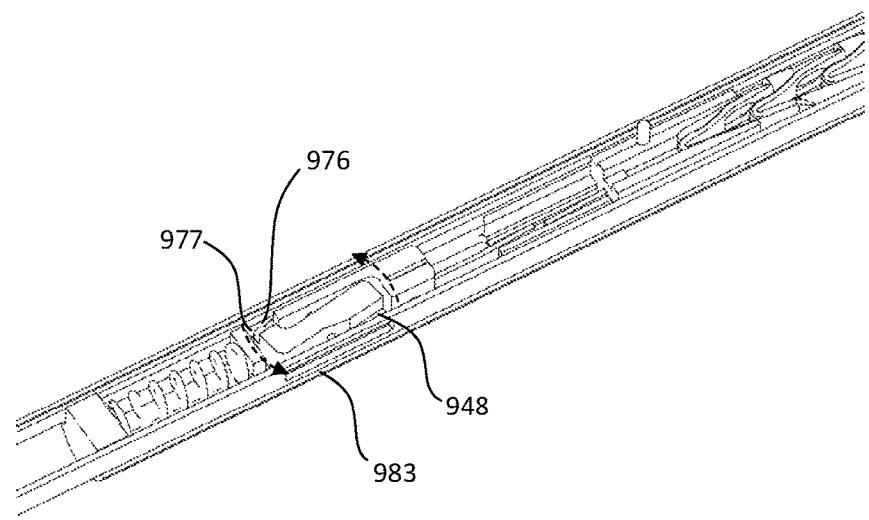
FIG. 27 shows release.

FIG. 27 shows release. Once the release bulge 976 reaches the release slope 977, release bulge 976 is pushed laterally and removes the hook 948 out of the hook slot 983.

Figure 28:
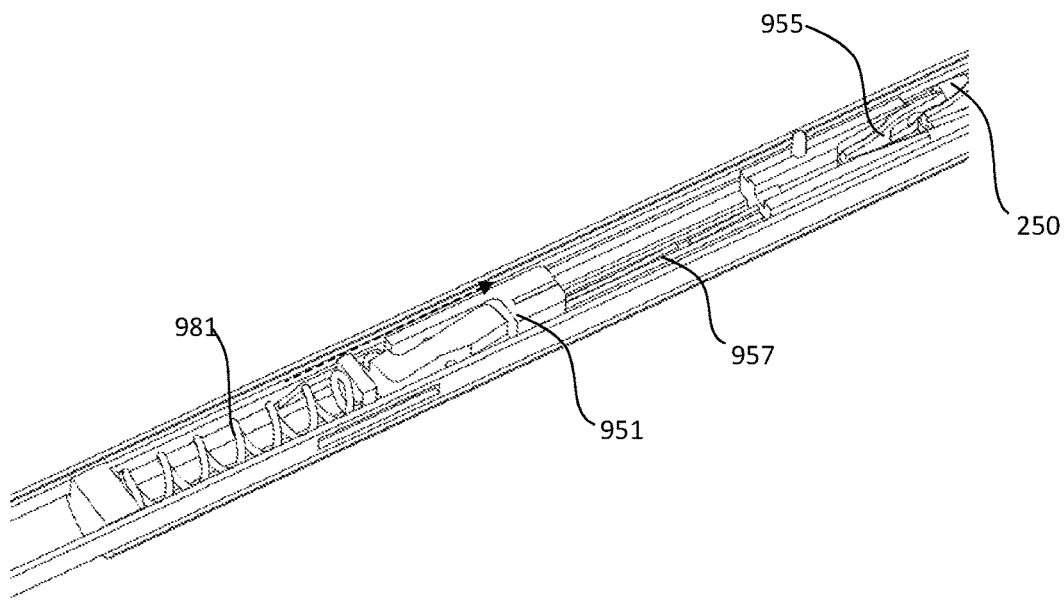
FIG. 28 shows advancement of the fastener.

FIG. 28 shows advancement of the fastener 250. The compressed spring 981 pushes the comb driver 951 and the drive comb 957 forward while advancing the entire fastener stack 955.

During operation, the fastener 250 is delivered by pushing each of its ends into tissue. As shown above, delivery is coordinated by the independent translation of push rods operably coupled to hook insertion member 252 and loop insertion member 357, which is triggered through the use of trigger 105. Coordination of delivery involves extending hook end of the fastener 250 away from applicator section 101 while also extending loop end of the fastener 250 and bringing the two ends of the fastener together (e.g., through the operation of a shape memory material in loop insertion member 357). Methods include using the needles to drive the fastener 250 into tissue and retracting the needles so they disengage from the fastener 250 leaving it in place and fastened in a closed loop, closing the wound.

The invention also provides methods for securing a medical prosthesis to tissue. Securing the prosthesis is accomplished through delivering a fastener to a target tissue that has a prosthesis applied to it, using applicator 100. Methods include inserting a distal portion of fastening device 100 into a patient's abdominal cavity through a trocar or through an incision. The distal end is pressed against the hernia mesh and a fastener is delivered through the tissue and hernia mesh and secured in place by pressing trigger 105 on handle 102. Shaft 103 is then removed.

Delivery according to the methods of the invention causes the first end of the body to mate with and be retained by the second end of the body, thereby forming the fastener into a closed configuration and securing the prosthesis to the tissue. The prosthesis can be secured by employing a fastening structure provided by the first and second members.

During delivery, hook insertion member 352 interfaces with second member 252 via needle interface hook 271. Loop insertion member 357 extends from insertion tube 356 and similarly interacts with first member 253 via loop interface hook 261.

Loop insertion member 357 is extended out from applicator section 101 and curves to guide the fastener through the prosthesis. Delivery is coordinated by the independent translation of push rods (discussed above) operably coupled to hook insertion member 252 and loop insertion member 357. Coordination of delivery involves extending hook end of the fastener 250 away from applicator section 101 while also extending loop end of the fastener 250 and bringing the two ends of the fastener together (e.g., through the operation of a shape memory material in loop insertion member 357). Methods can include pushing a fastener through a back surface of needle interface hook 271 and loop interface hook 261 with a corresponding insertion needle. The needles can drive the fastener 250 into the prosthesis (e.g., hernia mesh). The needles are then retracted, leaving the fastener 250 in place and fastened in a closed loop securing the prosthesis to the tissue.

One insight of the invention is that in hernia mesh 400 fixation, it is important that a fastener should be anchored to a fascia layer. Fascia is a layer of fibrous tissue containing closely packed bundles of collagen. Fascia provides a connective tissue that surrounds muscles, groups of muscles, blood vessels, and nerves. This is the layer to which surgeons affix a hernia mesh and the fastener design should form a strong anchor to that layer.

In each patient the thickness of the pre-peritoneal fat layer is different. For example, the first fascia layer in obese patients is significantly deeper than in slim patients. Some existing fixed-length hernia tacks favor shorter lengths so that, in slim patients, they will not penetrate all the way through the abdominal wall and to the skin. Fasteners that are too small, however, will not anchor into the fascia in some sites or in obese patients for whom the pre-peritoneal fat layer is substantially thick. One insight of the invention is that there is a need for variable depth fasteners that can be delivered by a single device to accommodate variations in the abdominal wall of different patients and variation in areas of the abdominal wall at any treatment site. A fastening device of the invention is provided that can fix a hernia mesh despite variations in tissue with fasteners that pass beyond the hernia mesh by a controlled amount (e.g., between about 3 millimeters and 15 millimeters). By provided fasteners that extended only about a couple of millimeters past the hernia mesh, a fastening device of the invention provides good fixation to prevent recurrence of the hernia. By avoiding use of a fastener that is too long, post-operative pain is minimized. Considerations in fastener operation are discussed in Abhishek, et al., 2012, Laparoscopic Umbilical Hernia Repair: Technique Paper, ISRN Minimally Invasive Surgery, pp. 1-4, Article ID 906405, and in Nguyen, et al., 2008, Postoperative Pain After Laparoscopic Ventral Hernia Repair: a Prospective Comparison of Clips Versus Tacks, JSLS 12:113-116, the contents of each of which are incorporated by reference.

In certain embodiments, a leading edge of either or both of the insertion needles is at least partially sharpened to aid in penetration of tissue. Each of needle interface hook 271 and loop interface hook 261 can have a back surface that gets pushed by the corresponding insertion needle. Alternatively or additionally, either needle interface hook can include a slot and a portion of the corresponding insertion needle can be dimensioned to engage the slot. By these means, the needles can drive the fastener 250 into tissue and when the insertion needles are retracted, they disengage with the fastener 250 leaving it in place and fastened in a closed loop.

Figure 29:
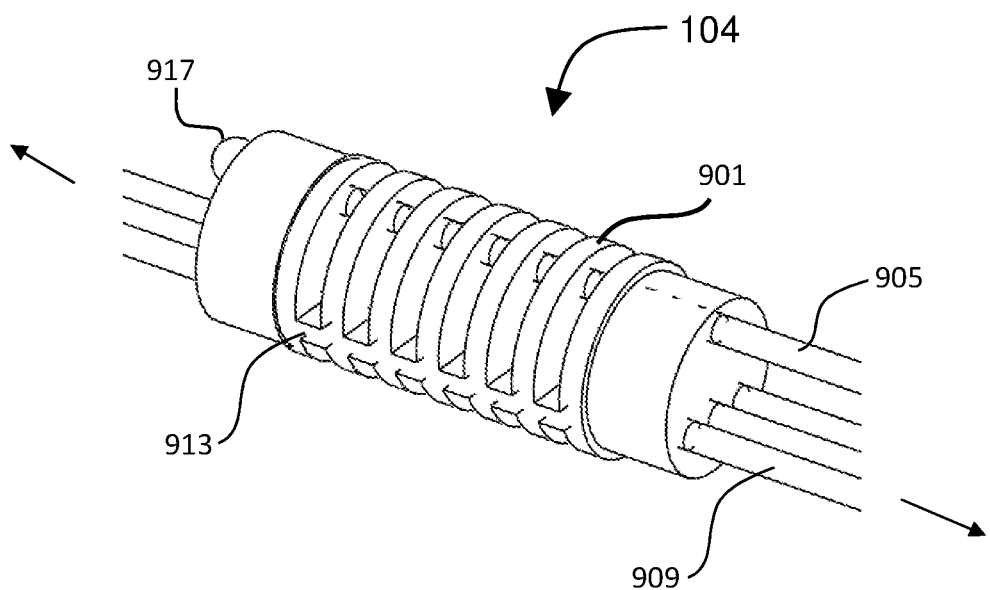
FIG. 29 shows the articulation joint.
Figure 30:
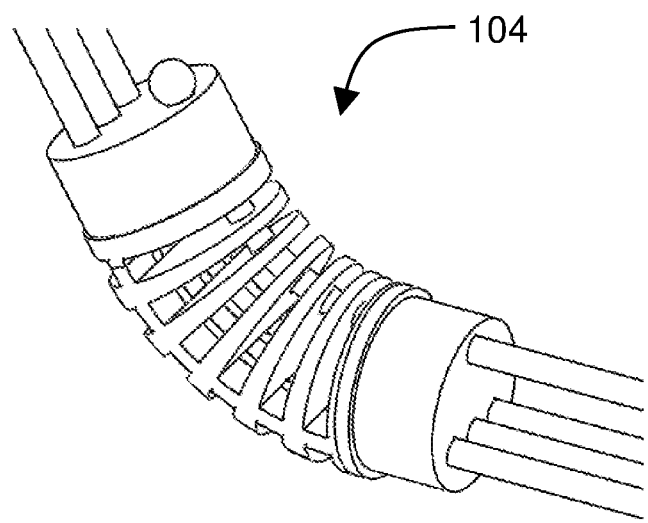
FIG. 30 shows a bend in the shaft of the device.

With reference to FIG. 2, applicator section 101 and shaft 103 can include articulation joint 104. FIGS. 29 and 30 show a structure by which articulation joint 104 can allow shaft 103 to bend while still operating according to the embodiment described herein.

FIG. 29 shows that articulation joint 104 includes a plurality of living hinge 913. A living hinge 903 generally includes a flexible portion and a flange 901. One or more of push rod 909 extend through joint 104 generally disposed so that, where there are multiple push rods, an axis of each push rod exhibits the same radius as the others when hinge 104 is bent. Flange 901 can be provided to limit the radius of curvature of hinge 104 to optimize functionality of applicator section 101, for example, by preventing the push rods from being bent too much.

Hinge 104 further includes an articulation cable 905 with an articulation wire ending 917 disposed on a distal side of hinge 104 from handle 102 (not pictured). When articulation wire 917 is pulled by a mechanism in handle 102 (discussed in more detail below), articulation wire ending 917 exhibits a compressive force on hinge 104, causing it to compress on one side, while expanding on the other, thus forming a bend in shaft 103.

FIG. 30 shows a bend in shaft 103. Articulation joint 104 can be made with any suitable material known in the art such as, for example, an elastically deformable material. In certain embodiments, the material is a low friction material such as PTFE to minimize friction between joint 104 and push rod 909.

The fastening device is designed and dimensioned for use in laparoscopic or endoscopic surgery. Shaft 103 is dimensioned for use with endoscopic tubes and apparatuses. The device can also be inserted through an incision or trocar and used within a body. In certain embodiments, fastening device 100 can hold at least one of the fastener 250 in a cartridge 801 that can be interchangeably loaded into applicator section 101 of fastening device 100.

Figure 31:
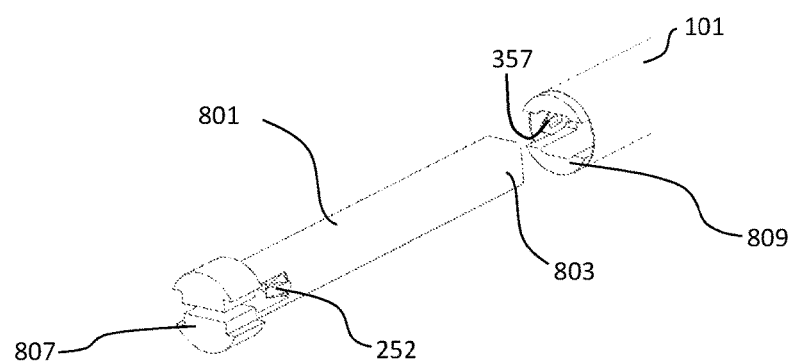
FIG. 31 shows a cartridge-style carrier for fasteners.

FIG. 31 shows a cartridge-style carrier 801 having an insertion end 803 and a spacer 807 oriented for insertion into applicator section 101. At the end of applicator section 101, FIG. 31 shows receiving pad 809 with loop insertion member 357 visible disposed therein. As can be seen depicted in the distal end of cartridge 101, second member 252 (specifically, a portion of needle interface hook 271) is held in a slot, oriented to interface with hook insertion member 352 in applicator section 101. Receiving pad 809 can include an interior shape dimensioned to receive insertion end 803.

Cartridge-style carrier 801 has a structure that cooperates with the mechanical structure of fastening device 100 so that the device can deliver and fasten fasteners within a body of a patient. Cartridge-style carrier 801 accommodates fasteners of different sizes.

In some embodiments, cartridge 801 uses an interchangeable spacer and spacers of different sizes accommodate different fasteners. In certain embodiments, each cartridge holds a number of fasteners of the same size. Spacers are provided to control the distance between the tip of the device and the tissue (or prosthesis) surface. For example, for smaller fasteners, a larger spacer is provided to prevent the fastener from penetrating too deeply into the tissue. Similarly, for larger fasteners, a smaller spacer allows for good penetration depth of the fastener.

Figure 32:
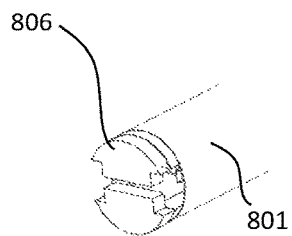
FIG. 32 shows a thin spacer for use with larger fasteners.

FIG. 32 shows a thin spacer 806 for use with larger fasteners. In some embodiments, the spacers are not interchangeable but instead formed as part of a disposable cartridge 801.

Figure 33:
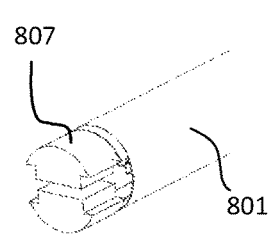
FIG. 33 shows a spacer for use with intermediate fasteners.

FIG. 33 shows a spacer 807 for use with intermediate fasteners.

Figure 34:
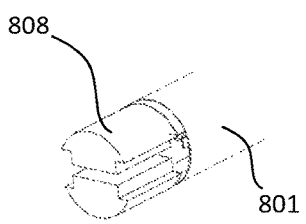
FIG. 34 shows a long spacer for use with small fasteners.

FIG. 34 shows a long spacer 808 for use with small fasteners. As shown in FIGS. 31-34, a spacer may include a fastener release slot disposed at an end of the body of the cartridge. In certain embodiments, cartridge 801 can be inserted into an end of an shaft 103 via insertion end. Spacers 806, 807, and 809 each provide a part of a fastener carrier operably connected to and at least partially disposed within shaft 103 and carrying a plurality of the fastener 250.

As can be seen in FIG. 31, when cartridge-style carrier 801 is inserted into shaft 103, second member 252 makes contact with hook insertion member 352 via needle interface hook 271 and first member 253 makes contact with loop insertion member 357. The fastener 250 is delivered to tissue by the action of push rods that drive the insertion needles. Each push rod, and thus each needle, translates parallel to an axis of shaft 103 relative to each other as well as to member 103. In some embodiments, the fasteners are stacked one on top of the other inside cartridge 801; during each fastener application cycle, a single fastener is connected to the said insertion needles and then inserted into the tissue. At the end of the application cycle, a fastener is advanced to the top of the cartridge in preparation to the next application cycle. In another embodiment cartridge-style carrier 801 includes an indicator which visually indicates to the surgeon the quantity of fasteners that remains in the cartridge. Motion of the push rods is governed by the mechanical structure of applicator 100.

Where shaft 103 includes articulation joint 104, articulation knob 106 controls the flexure of joint 104. Knob 106 is rotated by a user (e.g., with a thumb). During the rotation, articulation cable 905 (shown in FIGS. 29 & 30) is wrapped around the knob's axis, pulling it toward the handle, articulating joint 104. Knob 106 can include one or more of socket 139 adapted to fit a ball plunger in place once a desired degree of articulation is obtained.

The invention further provides methods for closing a wound that involve deploying fastening device 100 to deliver a fastener to a wound. Wound closure according to methods of the invention involves positioning the delivery tip close to the wound. Where the wound is inside the body, the shaft 103 is inserted through an incision, trocar, or endoscopic channel. A fastener is delivered and formed into a closed configuration by device 100.

When a practitioner depresses trigger 105, loop insertion member 357 extends from insertion tube 356 and interacts with first member 253 via loop interface hook 261. Hook insertion member 352 has and maintains a substantially straight conformation as it assists in driving a hook end of the fastener 250 into tissue. When loop insertion member 357 is extended out from applicator section 101, it curves to guide the fastening of the fastener.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for delivering a plurality of surgical fasteners, one at a time, into tissue of a patient, the device comprising:
a handle including a trigger;
a shaft extending from the handle and dimensioned for insertion into a patient's abdomen through an incision in the abdomen;
an applicator section at a distal end of the shaft, the plurality of fasteners disposed within the applicator section, each of the plurality of fasteners formed as a single piece comprising a hook at one end and a loop at the other end; and
first and second members operably coupled to the trigger whereby activation of the trigger by a user causes
the first member to engage the loop of one of the fasteners carry the loop through the patient's tissue,
the second member to engage the hook of that fastener, carry the hook through the tissue, and pass the hook through the loop, thereby locking the fastener into a closed loop in the tissue while the loop remains engaged by the first member, and
the first and second members to retract into the applicator section leaving the closed fastener in the tissue.

2. The devices of claim 1, wherein the shaft is dimensioned for insertion into the abdomen through a trocar placed in the incision.

3. The device of claim 2, wherein a distal tip of the first member defines a pair of prongs configured to be inserted into a recess at a distal end of the loop of the fastener.

4. The device of claim 3, wherein the pair of prongs is disposed together in the recess when inserted into the recess.

5. The device of claim 4, wherein the distal tip of the first member is configured to define an opening corresponding to the loop while the pair of prongs is held together by the recess.

6. The device of claim 5, wherein the distal tip of the first member comprises a super-elastic material that biases the pair of prongs together, and being withdrawn from the recess the pair of prongs are opened by being dragged over the second member.

7. The device of claim 6, wherein the super-elastic material comprises nickel titanium alloy.

8. The device of claim 6, wherein retraction of the first member includes removing the pair of prongs from the recess and withdrawing the distal tip of the first member by allowing the hook end of the fastener to pass through the gap between the pair of prongs.

9. The device of claim 3, wherein at least one of the first and second members comprises a flexible, pre-shaped portion that moves along a curved path.

10. The device of claim 9, wherein the flexible portion remains straight when disposed in the shaft and, upon the activation of the trigger, extends from the shaft and moves along the curved path by assuming a curved shape.

11. The device of claim 10, wherein the at least one of the first and second members moves along a straight path and the curved path.

12. The device of claim 10, wherein the first and second members are operably coupled to the trigger by first and second push rods, wherein each push rod comprises a distal end engaged with its respective member and a proximal end engaged with a slot wheel in the handle.

13. The device of claim 12, wherein the applicator section is configured to receive a cartridge loaded with the plurality of fasteners.

14. The device of claim 13, wherein the cartridge is from a set of cartridges, at least two of the cartridges in the set carrying fasteners of a different size.

15. The device of claim 14, wherein the device is configured to deliver fasteners of different sizes to different penetration depths within the patient's tissue.

16. The device of claim 10, wherein the first and second members are configured to penetrate a prosthetic mesh and the patient's tissue.

17. The device of claim 10, wherein the pair of prongs assumes a closed configuration when disposed within the recess.

18. The device of claim 17, wherein the closed configuration of the prongs defines a hoop-like structure corresponding to the loop while the pair of prongs is disposed within the recess.

19. The device of claim 18, wherein the distal tip of the first member comprises a super-elastic material that biases the pair of prongs together, and the pair of prongs spread apart from one another while being retracted due to being drawn over the fastener or second member.

20. The device of claim 19, wherein the super-elastic material is a nickel-titanium alloy.

21. The device of claim 18, wherein the distal tip of the first member comprises a material that biases the pair of prong apart from one another such that upon being withdrawn from the recess the pair of prongs springs open to define a gap between the pair of prongs.

22. The device of claim 21, wherein retraction of the first member includes removing the pair of prongs from the recess and withdrawing the distal tip of the first member by allowing the hook end of the fastener to pass through the gap between the pair of prongs.

* * * * *